United States Patent
D'Andrea

(10) Patent No.: US 9,320,915 B2
(45) Date of Patent: *Apr. 26, 2016

(54) BRACHYTHERAPY TANDEM AND OVOID IMPLANTATION DEVICES AND METHODS

(71) Applicant: Mark A. D'Andrea, Houston, TX (US)

(72) Inventor: Mark A. D'Andrea, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 14/613,038

(22) Filed: Feb. 3, 2015

(65) Prior Publication Data

US 2015/0157878 A1  Jun. 11, 2015

Related U.S. Application Data

(63) Continuation of application No. 13/478,794, filed on May 23, 2012, now Pat. No. 8,979,725.

(51) Int. Cl.
*A61N 5/10* (2006.01)
*A61B 18/04* (2006.01)
*A61B 18/00* (2006.01)

(52) U.S. Cl.
CPC ............ *A61N 5/1016* (2013.01); *A61N 5/1067* (2013.01); *A61N 5/1071* (2013.01); *A61B 18/04* (2013.01); *A61B 2018/00559* (2013.01); *A61B 2018/046* (2013.01); *A61N 2005/1094* (2013.01)

(58) Field of Classification Search
CPC . A61N 5/1001; A61N 5/1007; A61N 5/1014; A61N 5/1016; A61N 2005/1008
See application file for complete search history.

(56) References Cited

U.S. PATENT DOCUMENTS 3,060,924 A    10/1962  Rush
4,292,960 A *  10/1981  Paglione ........................... 600/2
(Continued)

FOREIGN PATENT DOCUMENTS

EP    1 568397 A1    8/2005

OTHER PUBLICATIONS

Horton, John et al., LDR Intracavitary Brachytherapy Applicators, UT MD Anderson Cancer Center Intracavitary Brachytherapy, 2005.
(Continued)

*Primary Examiner* — Charles A Marmor, II
*Assistant Examiner* — Thaddeus Cox
(74) *Attorney, Agent, or Firm* — Cook Alex Ltd.

(57) ABSTRACT

Intracavitary brachytherapy tandem and ovoid oncology treatment systems and methods are provided. One such system and method employs a multi-part tandem having a detachable distal section suitable for retaining within a body cavity such as the uterus, both during radiation treatment and during recovery time between radiation treatments. This distal portion can be intended for single-patient use and be disposed of after completion of a radiation treatment session having multiple radiation dose treatment times. One or both of real time in vivo detection and monitoring and hypertherapy features can be included. One or more of the system tandem or ovoid colpostats feature bendability to tailor the system to the specific body and patient being treated. The method includes having a tandem distal section inserted into a body cavity such as a uterus and remaining within the body cavity in between treatment times. Other systems and methods incorporate balloon devices that assist in spacing radiation doses away from body sites at which radiation treatment is not intended. Balloon devices also can be provided for adjusting and maintaining separation spacing between two ovoid colpostats while intracavitary.

4 Claims, 20 Drawing Sheets

(56) References Cited

U.S. PATENT DOCUMENTS

| | | | |
|---|---|---|---|
| 4,294,264 | A | 10/1981 | Fischell et al. |
| 4,434,789 | A | 3/1984 | Kumar |
| 4,448,198 | A | 5/1984 | Turner |
| 4,798,215 | A | 1/1989 | Turner |
| 4,947,842 | A | 8/1990 | Marchosky et al. |
| 4,967,765 | A | 11/1990 | Turner et al. |
| 5,012,357 | A | 4/1991 | Schoeppel et al. |
| 5,249,585 | A | 10/1993 | Turner et al. |
| 5,429,582 | A | 7/1995 | Williams |
| 5,520,646 | A | 5/1996 | D'Andrea |
| 5,562,594 | A | 10/1996 | Weeks |
| 5,653,683 | A | 8/1997 | D'Andrea |
| 5,720,717 | A | 2/1998 | D'Andrea |
| 5,913,813 | A | 6/1999 | Williams et al. |
| 6,017,322 | A * | 1/2000 | Snoke et al. ............... 604/95.01 |
| 6,083,148 | A | 7/2000 | Williams |
| 6,312,375 | B1 | 11/2001 | Montebello et al. |
| 6,413,204 | B1 | 7/2002 | Winkler et al. |
| 6,482,142 | B1 | 11/2002 | Winkler et al. |
| 6,699,171 | B2 | 3/2004 | Harmon |
| 6,866,624 | B2 | 3/2005 | Chomenky et al. |
| 7,447,550 | B2 | 11/2008 | Eggers et al. |
| 7,534,202 | B2 | 5/2009 | Eng |
| 7,556,596 | B2 | 7/2009 | Mourtada et al. |
| 7,651,458 | B2 | 1/2010 | Mourtada et al. |
| 7,666,130 | B2 | 2/2010 | Mick |
| 8,033,979 | B2 | 10/2011 | Mick |
| 8,423,152 | B2 | 4/2013 | Turner et al. |
| 8,979,725 | B2 * | 3/2015 | D'Andrea ........................ 600/6 |
| 2003/0153803 | A1 | 8/2003 | Harmon |
| 2005/0251235 | A1 | 11/2005 | Schlorff et al. |
| 2006/0030914 | A1 | 2/2006 | Eggers et al. |
| 2006/0116546 | A1 | 6/2006 | Eng |
| 2006/0205992 | A1 * | 9/2006 | Lubock et al. ................... 600/3 |
| 2008/0064916 | A1 * | 3/2008 | Mick ................................. 600/6 |
| 2008/0086050 | A1 | 4/2008 | Misic et al. |
| 2008/0228063 | A1 | 9/2008 | Turner et al. |
| 2010/0100092 | A1 | 4/2010 | Turner et al. |
| 2010/0145132 | A1 * | 6/2010 | Isham ............................... 600/7 |
| 2011/0182880 | A1 | 7/2011 | Von Stein et al. |
| 2011/0200526 | A1 | 8/2011 | Parsal et al. |
| 2011/0224477 | A1 | 9/2011 | Issels |
| 2012/0123188 | A1 * | 5/2012 | Rahimian ......................... 600/6 |
| 2012/0172651 | A1 * | 7/2012 | Cutrer ............................... 600/4 |
| 2013/0177566 | A1 | 7/2013 | Ruben et al. |
| 2013/0261368 | A1 | 10/2013 | Schwartz |

OTHER PUBLICATIONS http://www.cancer.org/Treatment/TreatmentsandSideEffects/TreatmentTypes/hyperthermia, Downloaded May 2, 2012.

Research Spotlight, Eos, vol. 92, No. 33, Aug. 16, 2011.

Zhu, Timothy C., Diode Dosimetry for Megavoltage Election andPhoton Beams, Dept. of Radiation Oncology, U. of Pennsylvania, Philadelphia, PA, Jun. 24, 2009.

Dutta, Pinaki, MD et al., How is radiation therapy given?, OncoLink Cancer Resources, www.oncolink.org/treatment/article, Downloaded Oct. 28, 2011.

http://vantageoncology.com/centers2006/html/body/treatment/wildomar, High-Dose Rate Brachytherapy (HDR)andemandOvoid Implant,WildomarRadiation TherapyCentr, Download Oct. 31, 2011.

www.americanbrachytherapy.org/about Brachytherapy, What is Brachytherapy?, American Brachytherapy Society, Downloaded Nov. 4, 2009.

Section III: Disease Sites, Chapter 22: Uterine Cervix, textbook pp. 657-659, circa 2001.

BSD-500 Hyperthermia System brochure, BSD Medical Corpopration, 2007.

BSD-2000 Hyperthermia System, BSD Medical Corporation 2010.

The International Search Report and The Written Opinion, of PCT/US2013/042165, dated Aug. 21, 2013.

* cited by examiner

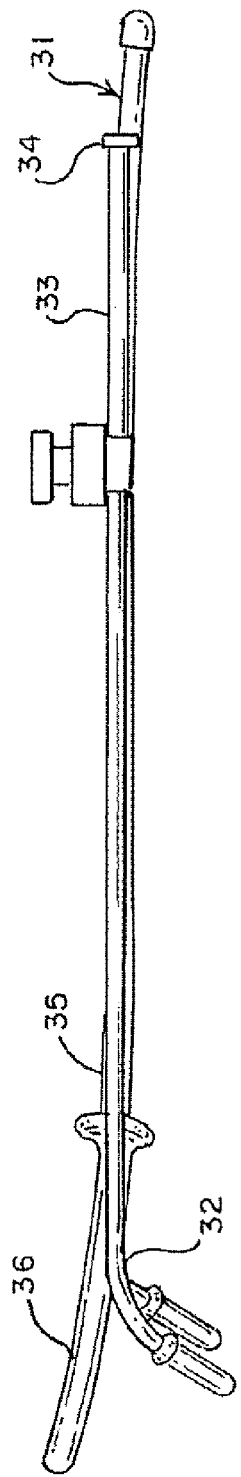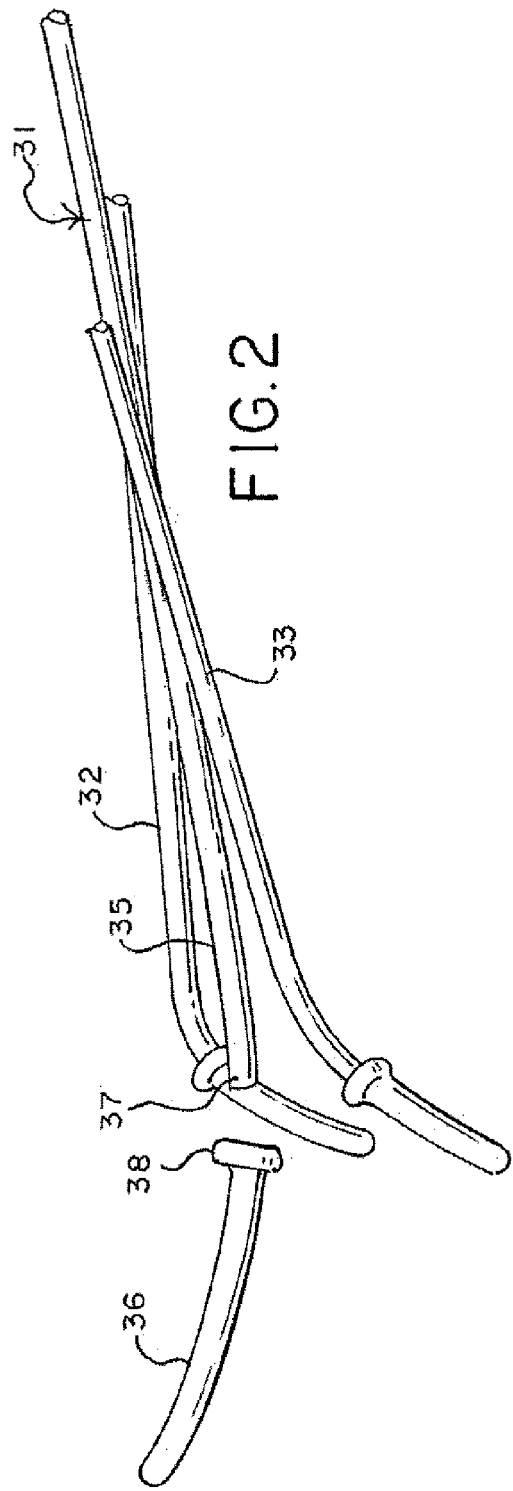

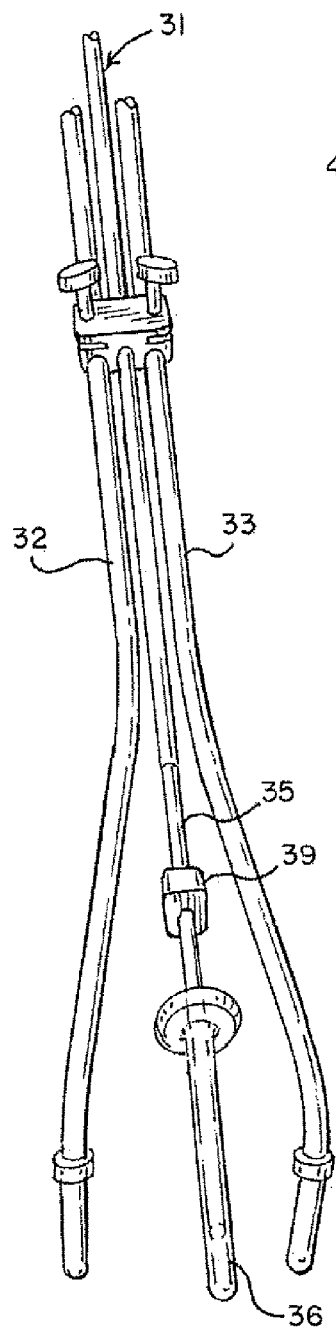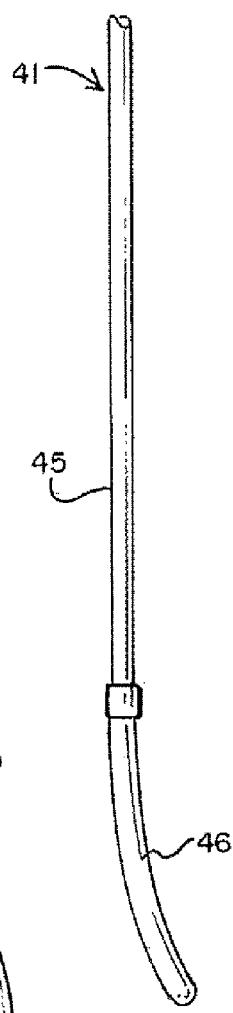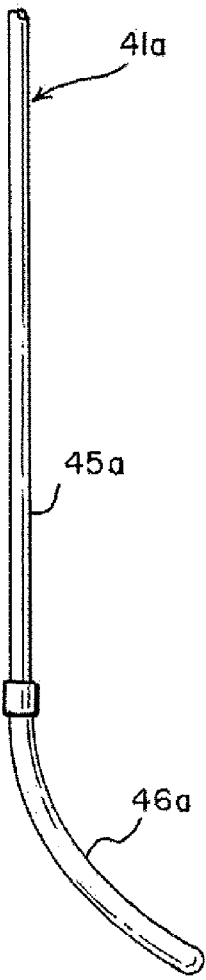

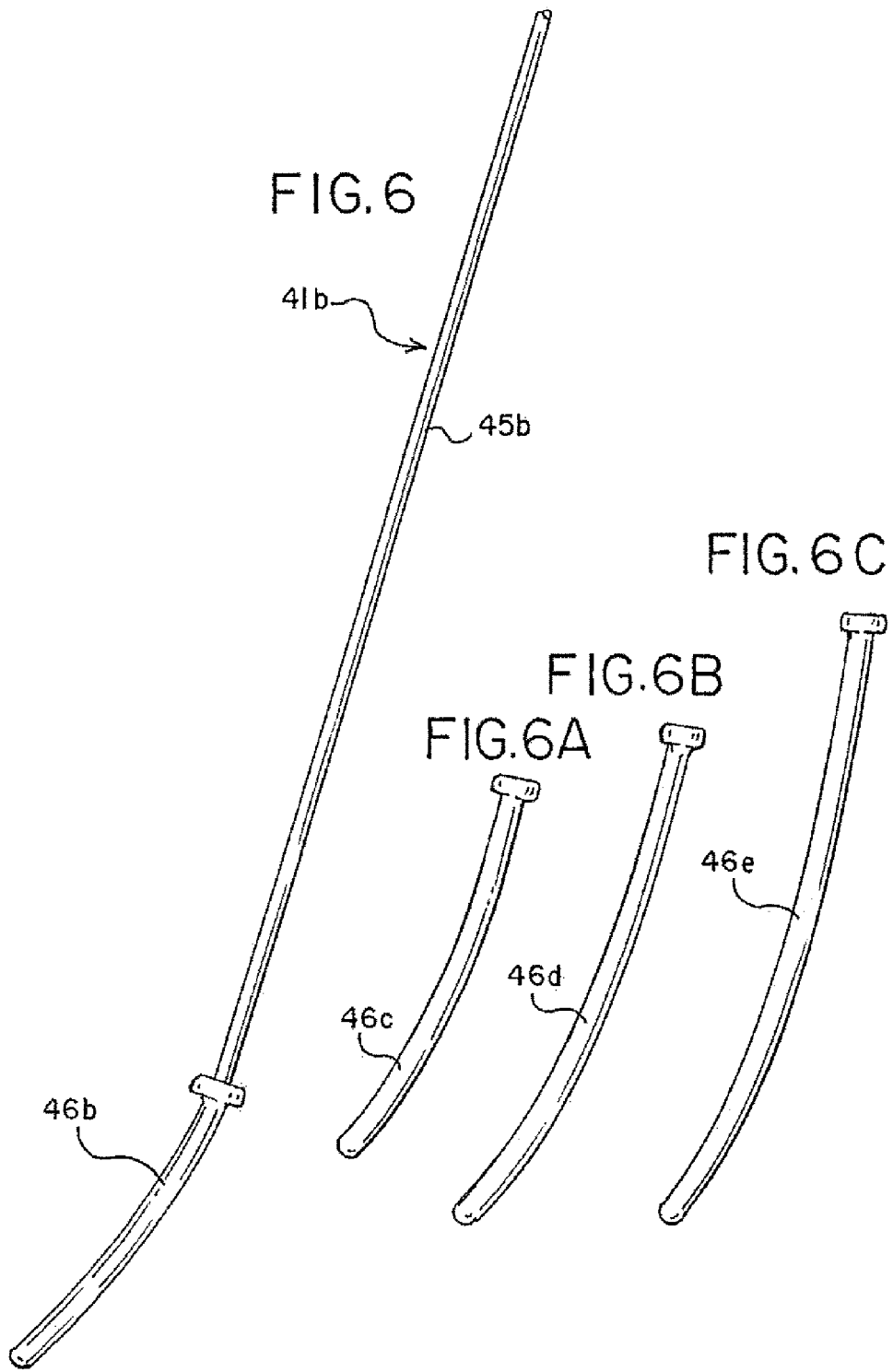

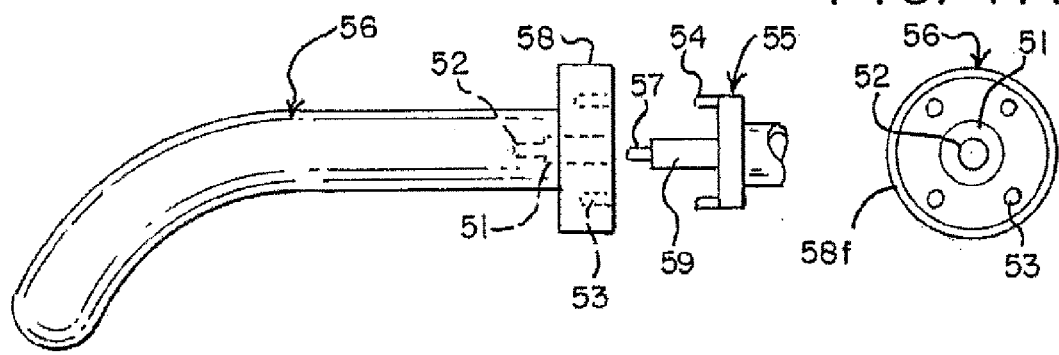
FIG. 7
FIG. 7A
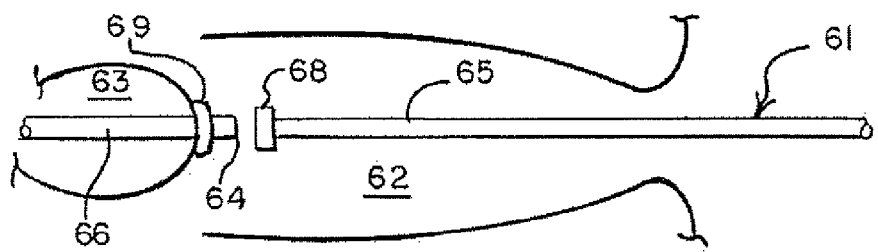
FIG. 8
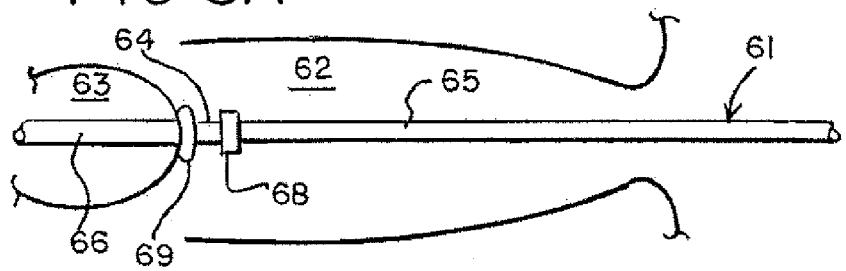
FIG. 8A

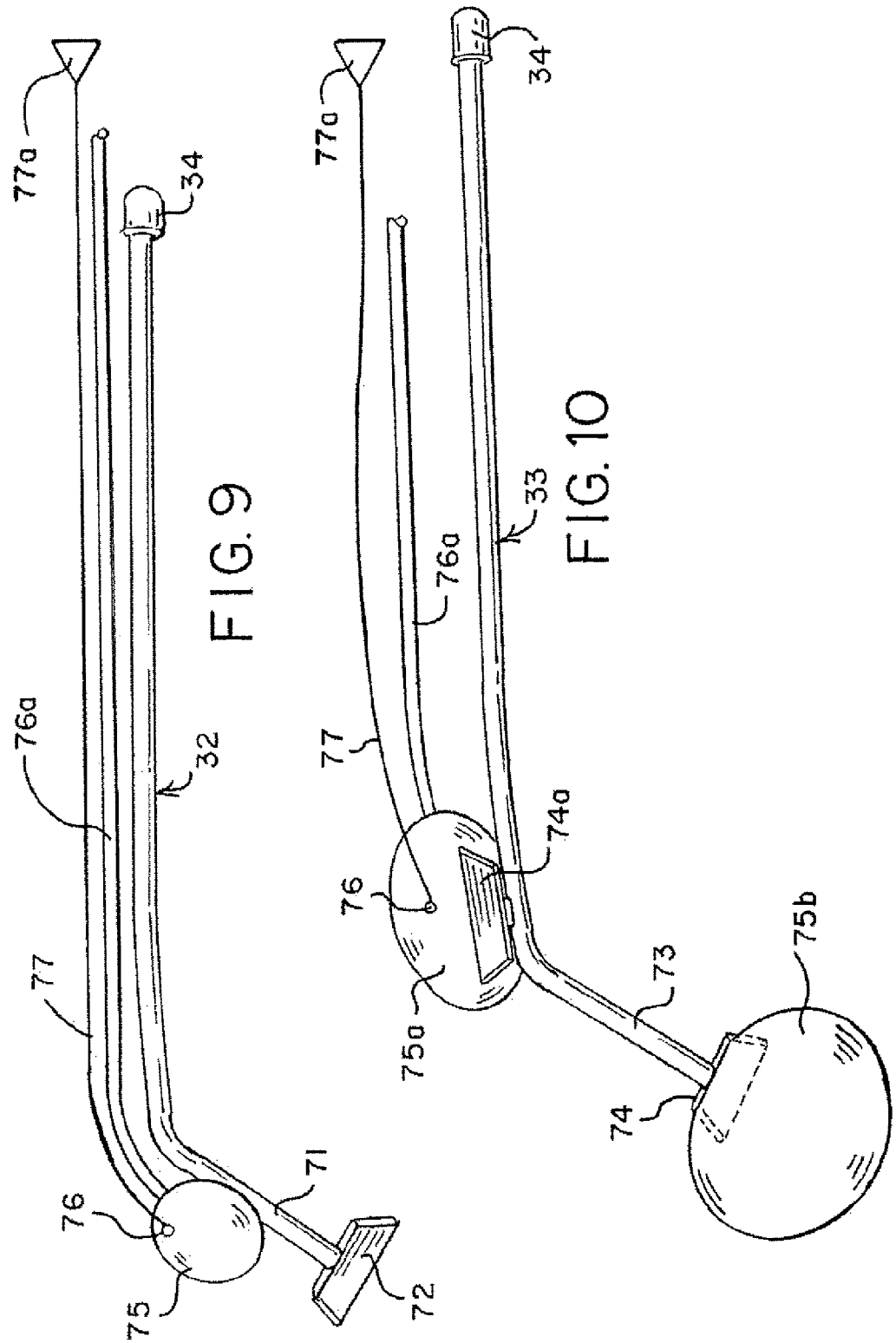

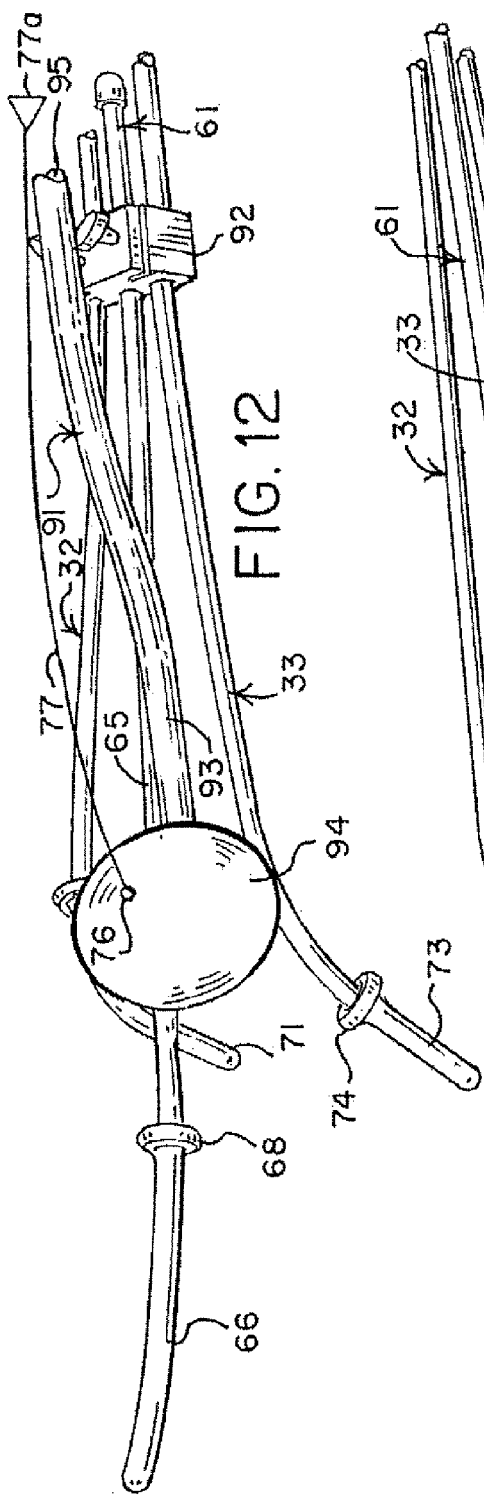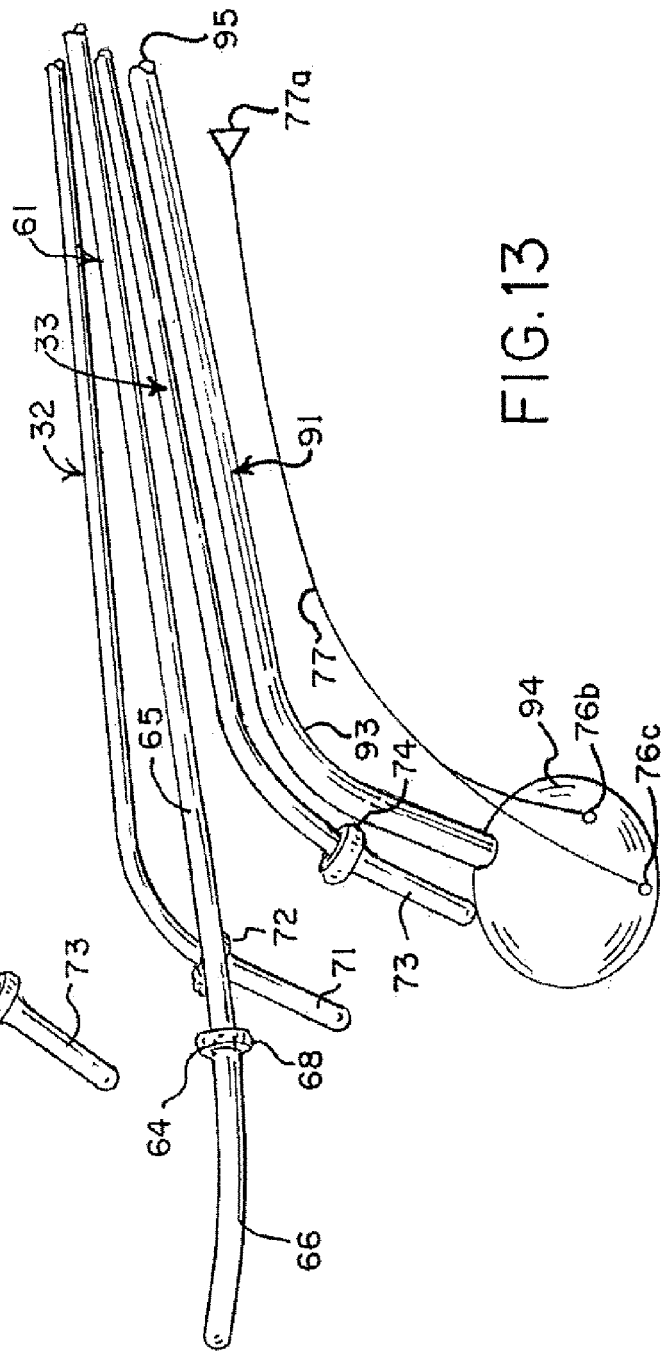

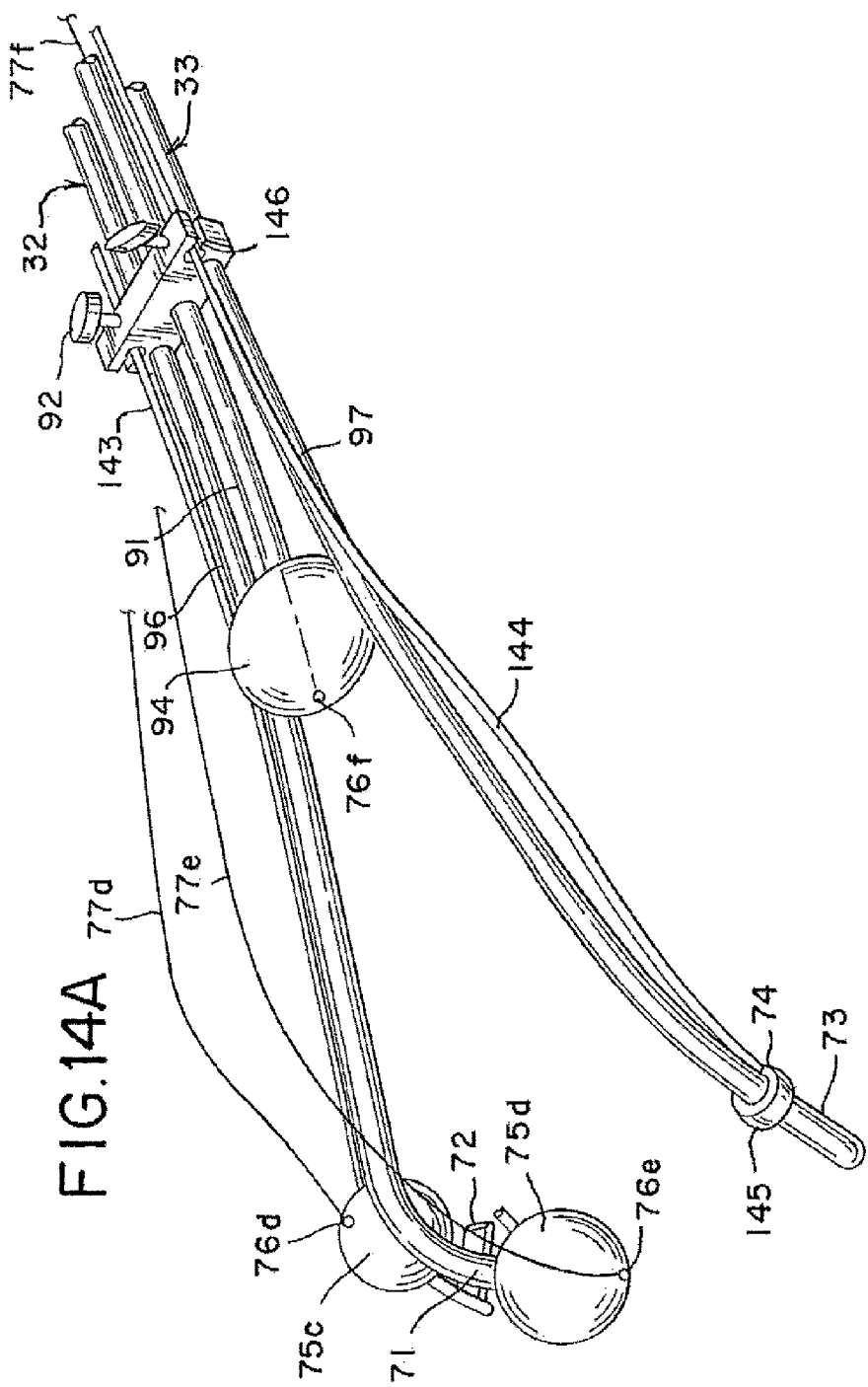

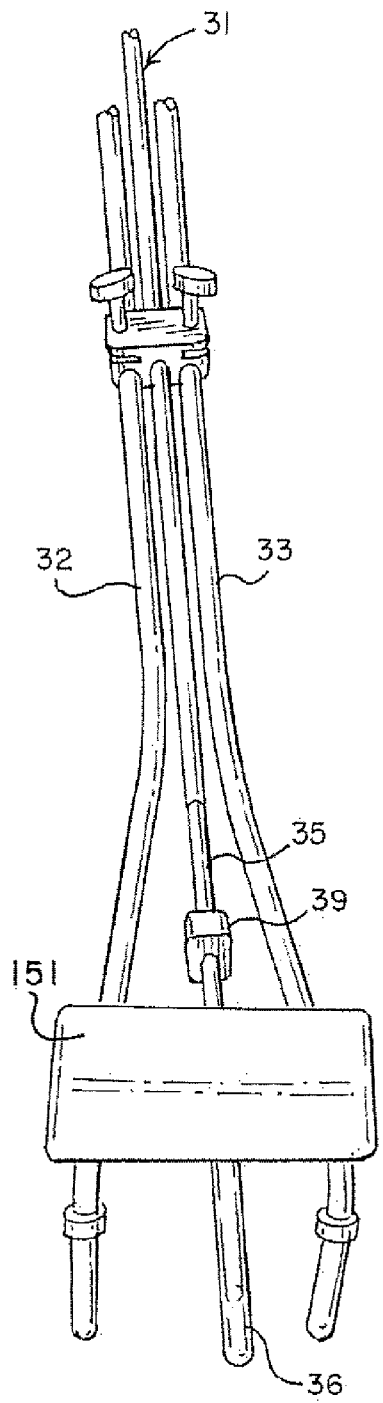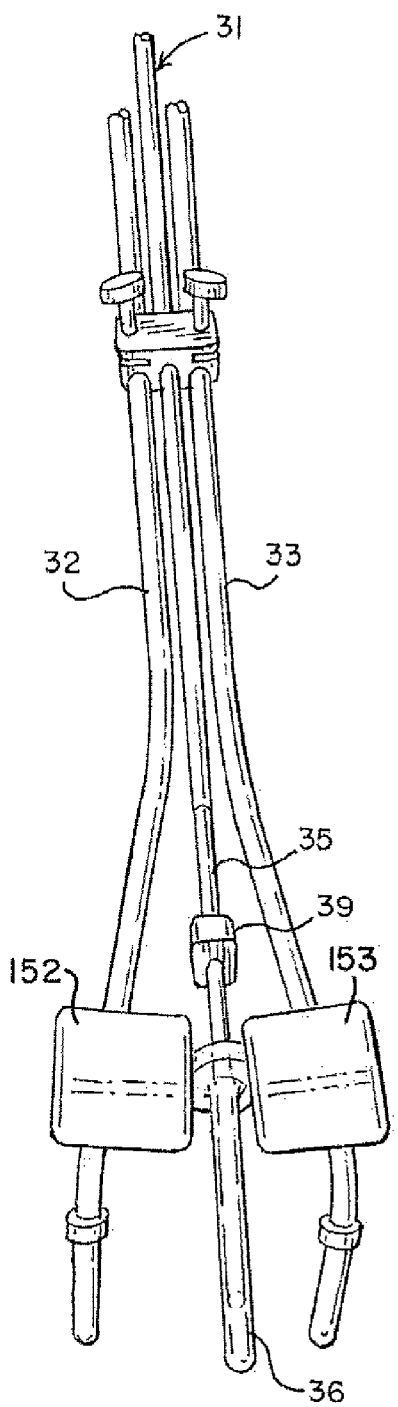

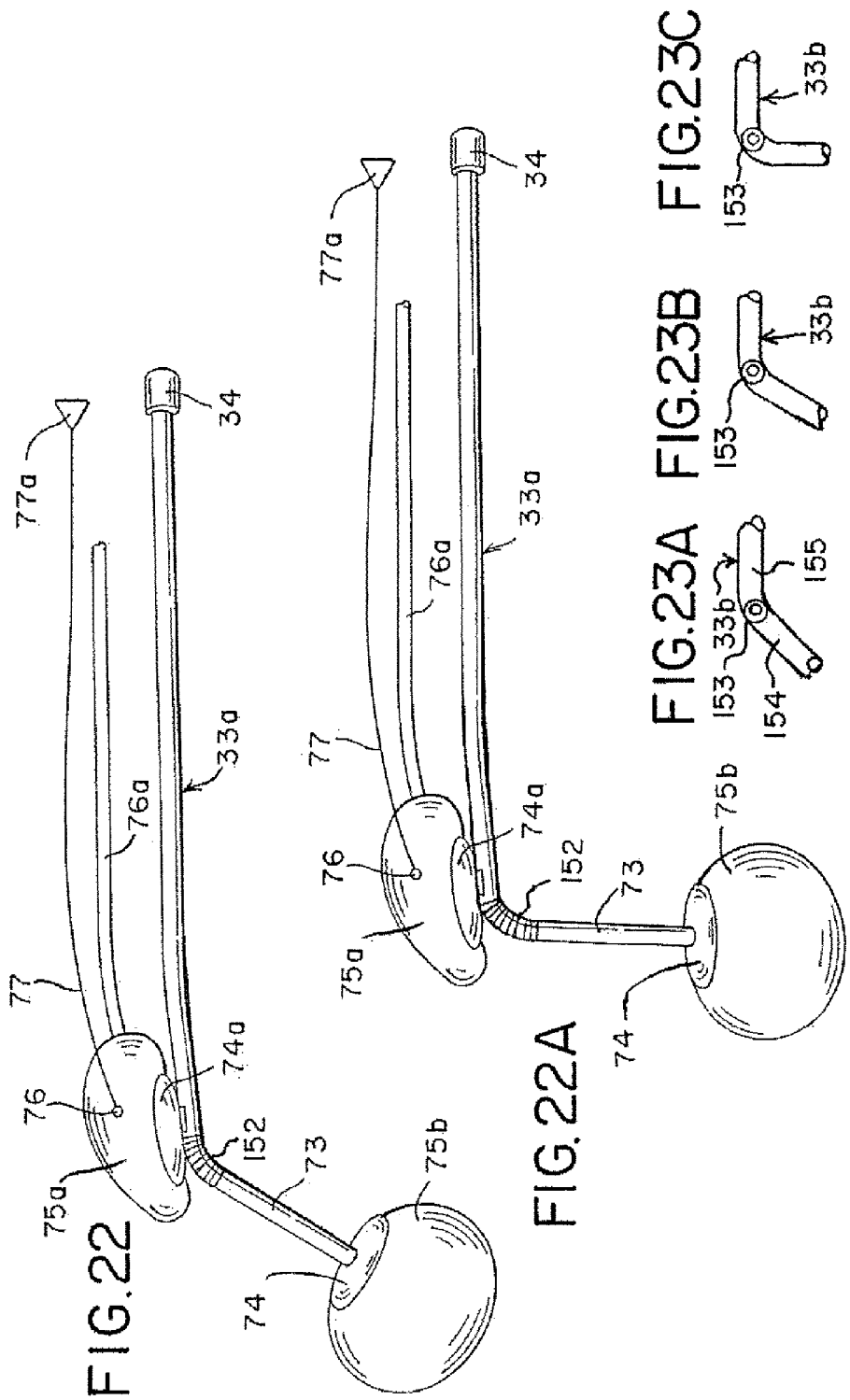

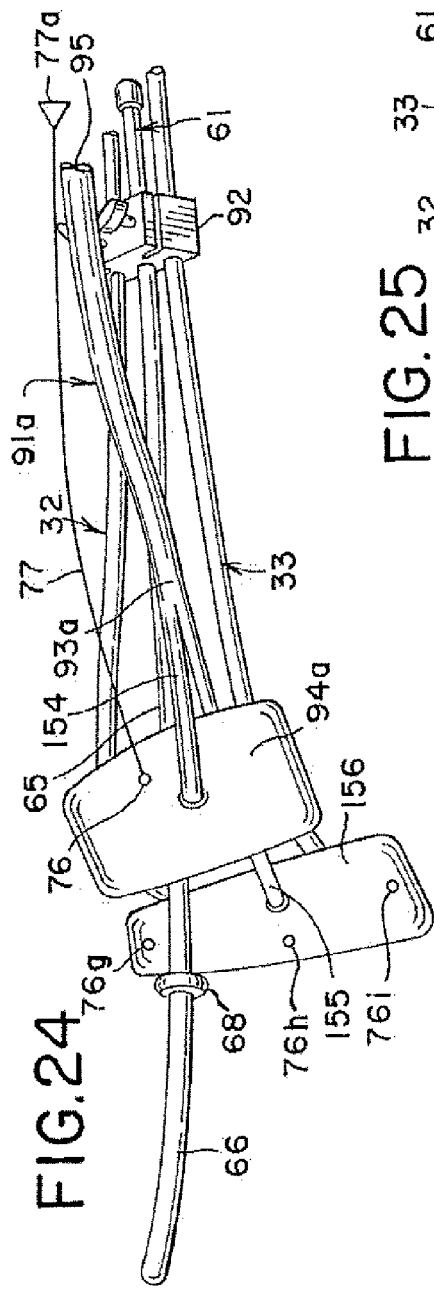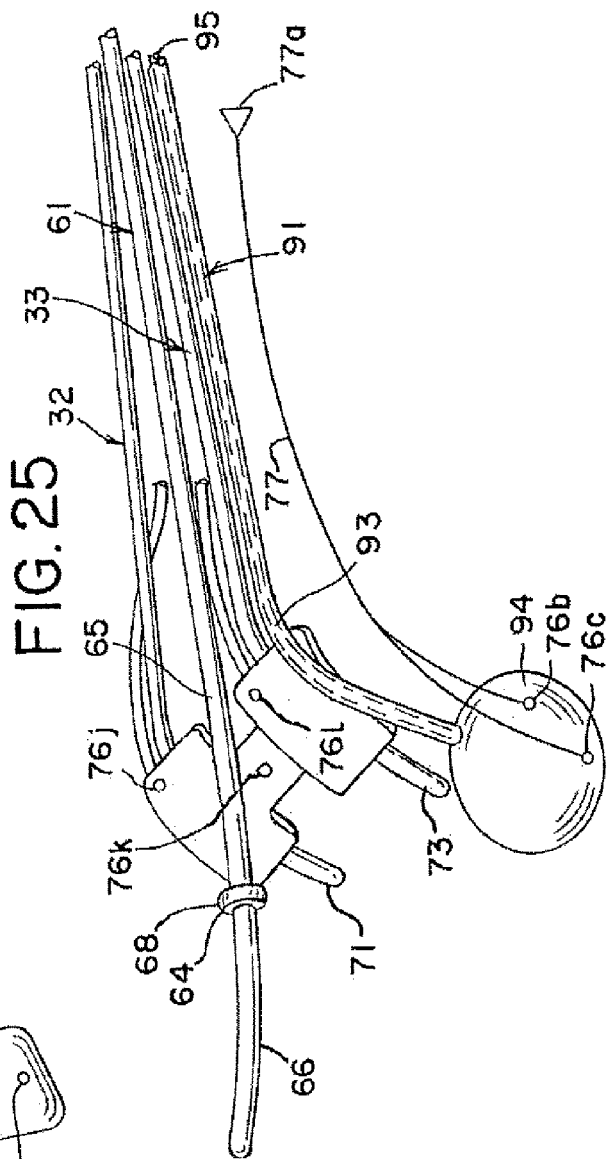

BRACHYTHERAPY TANDEM AND OVOID IMPLANTATION DEVICES AND METHODS

This application is a continuation of and claims the benefit of U.S. application Ser. No. 13/478,794, filed May 23, 2012, hereby incorporated by reference hereinto.

BACKGROUND

1. Field of the Disclosure

The present subject matter relates to vaginal and intrauterine brachytherapy tandem and ovoid implantation systems and methods employing same. More particularly, the present subject matter relates to such systems wherein the tandem has a detachable distal section that is disposable and intended for single-patient brachytherapy use, thereby allowing the single-patient distal section to maintain intracavitary placement for multiple treatment sessions and in between them, while the remainder of the system is removable in between these multiple treatment sessions.

2. Description of Related Art

Numerous devices and methods are known for intrauterine brachytherapy use. Many of these incorporate a tandem delivery tube and an ovoid colpostat. Often, dual ovoid colpostats are included and generally flank the tandem delivery tube. With this general approach, multiple delivery paths are available for treatment of different intrauterine locations.

Radiation oncology intracavitary brachytherapy practitioners and researchers have developed various systems. In the Manchester system, for example, a tandem and two ovoids are available in differing diameter sizes. In the Fletcher system, the ovoid colpostats have internal shielding, and polymer caps can be added to increase diameter. Different styles of tandems are available, having different curvatures and/or lengths, and a yoke attaches the tandem and ovoids together and facilitates maintaining proper positioning during treatment. Other systems include the Madison system, the Paris system and the Stockholm system. Typically in each of these systems, the tandem is inserted first, followed by the ovoids or other treatment components or devices. Typical treatment patterns or regimens follow multiple doses, and thus multiple intrauterine insertions and removals of the equipment are spaced apart in time by non-treatment intervals that vary depending upon the oncology protocol. Those application or treatment times typically vary between about five to twenty minutes. Usually the total treatment time is two or three days, with multiple treatments and non-treatment intervals proceeding during this timeframe.

Procedures for treating uterine or cervical carcinoma with tandem and ovoid systems and implant procedures typically follow a protocol calling for a series of three to seven implants, such as when following high dose rate (HDR) brachytherapy. At times, the oncologist may choose to use a low dose rate (LDR) brachytherapy regimen, typically based on cesium delivery as $^{137}$Cs. For HDR brachytherapy regimens $^{192}$Ir is frequently used because of its high specific activity. Other isotopes are available and used as warranted. The degree of treatment is measured in terms of units of radiation exposure (in roentgens or Gray or Gy) that are prescribed at specific points, termed A and B, within the pelvis. Details in this regard are known to radiation oncologists, medical physicists and other medical professionals experienced in brachytherapy. For example, in an early system (the Manchester system) point A can be at a location 0.2 cm lateral to the center of the uterine canal and 2 cm from the mucous membrane of the lateral fornix in the plane of the uterus. In that system, point B is defined as 0.5 cm from the patient's midline at the same level as point A. Point A can be considered a location of the paracervical triangle, while point B concerns the regional (Obturator) lymph nodes. An objective is to provide reasonably constant and predictable dose rates at each location, as applied by the isotopes of the tandem and ovoid system. An exemplary dose rate to be provided at point A is between about 50 and 55 cGy per hour. Specifics as to average doses at particular locations, such as point A and point B, generally are known to the medical professional.

Accordingly, it is clear that intracavitary brachytherapy such as that used in treating vaginal, uterine and cervical cancers needs to be exacting and specific in dose rates, durations and radiation target locations. Oncology treatment systems and methods such as tandem and ovoid combinations demand dosage rate and location precision during intrauterine brachytherapy. In addition, the closeness of tissues not intended to be irradiated should be taken into consideration. For example, it is important to minimize, if not eliminate, radiation exposure to the bladder and rectum. Generally, tandem and ovoid positions are noted on X-ray images in order to ensure intended placement and to allow the medical physicist or professional to generate a radiation treatment plan specific for this placement and for the particular anatomy and disease location and severity for the particular patient and for this treatment event.

It will be appreciated that tandem and ovoid colpostat delivery systems can be used in brachytherapy that is applied manually or remotely using remote afterloading systems. In remote afterloading systems, the radioactive materials are delivered from a safely contained source by way of hollow tubes to hollow portions of the tandem and ovoid components. Radioactive material can be in the form of wires or seeds. In such systems, the radioactive material is delivered via remote control, such as by operation of a motor, after the medical professionals all are removed from the treatment room. Such remote delivery equipment moves the radioactive dose into the applicator (such as an ovoid or other colpostat or tandem) already positioned within the body cavity.

SUMMARY

There are several aspects of the present subject matter that may be embodied separately or together in the systems, devices and methods described herein and claimed below. These aspects may be employed alone or in combination with other aspects of the subject matter described herein, and the description of these aspects together is not intended to preclude the use of these aspects separately or the claiming of such aspects separately or in different combinations as may be set forth in the claims appended hereto.

In one aspect, a system is provided for intracavitary or intrauterine brachytherapy, such being a tandem and ovoid implantation system having at least one tandem useful in connection with intercavitary oncology assemblies or systems, which tandem has a distal section detachably secured to the proximal section of the tandem. This detachable distal section is made of material suitable for single-patient brachytherapy use, such as being made of a disposable material, typically a polymeric material. The proximal section is made of durable material suitable for multiple-patient brachytherapy and repeated sterilizations. The system typically also includes at least one ovoid colpostat for intracavitary radiation dose delivery, with the tandem and ovoid colpostat being attachable together while delivering radiation dosage regimens to different intracavitary locations.

In another aspect, a method is provided that positions radiation sources via tandem and ovoid systems having a tandem with a detachable distal section and made of a material suitable for single-patient brachytherapy use and not made of durable material of the type that is suitable for multiple-patient brachytherapy and intended for repeated harsh sterilization between patient uses. Consistent with the method, the detachable distal section remains in its desired intracavitary location throughout the multiple dosing regimen for that particular patient, including between radiation dosing treatments, while some or all of the rest of the system is removed while actual radiation treatment is not being conducted.

In yet another aspect, a tandem has a distal section and a proximal section, these sections being selectively attachable and detachable to each other. The proximal section is made of durable material typical for medical devices intended for multiple-patient use and the rigors of sterilization between uses. The distal section, by contrast, is intended only for single-patient brachytherapy use, being made of material less durable than the proximal section and being structured and shaped so as to be suitable for extended intracavitary placement during a substantial portion of a hospital stay or outpatient radiation treatment. Such distal section may in fact be disposable.

In a further aspect, a brachytherapy tandem and ovoid implantation system includes at least one tandem and at least one ovoid colpostat, together with an intracavitary balloon member. In one aspect, the balloon component is a balloon and a shaft for inflating and deflating the balloon, the shaft being attached to the system.

Another aspect concerns intrauterine brachytherapy tandem and ovoid colpostat implantation systems and methods utilizing at least one tandem sized and structured for intracavitary and intrauterine deployment, the tandem having a detachable distal section made of material suitable for single-patient brachytherapy use, while the tandem proximal section is made of a durable material suitable for multiple-patient brachytherapy use. Adjacent end portions of the distal end proximal sections of the tandem are sized, shaped and structured to be attachable to and detachable from each other. At least one ovoid colpostat is provided that is sized and structured for intracavitary oncological dose delivery in coordination with the tandem. When desired, two ovoid colpostats are included and the tandem and colpostats are attached together by an attachment unit, whereby the tandem assists in properly positioning the brachytherapy system within the body of the patient for delivering intracavitary radiation doses. Typically, the ovoid colpostats flank the tandem along a substantial length of each.

In a further aspect, a brachytherapy system and method includes at least one intracavitary balloon component that is sized, shaped and positioned to impart a space separation between a radiation source of the system emanating from the colpostat or colpostats and an internal body location at which radiation treatment is not desired. Each balloon can be a separate unit provided in association with or secured to the tandem or an ovoid colpostat, or both. In other approaches, one or more balloons are secured to a colpostat or multiple colpostats and/or tandem.

According to another embodiment, an intrauterine brachytherapy method includes providing intrauterine brachytherapy tandem and ovoid colpostat, inserting a distal section of the tandem, unassembled to the rest of the tandem, within a patient's uterus, while a proximal end of this tandem distal section is accessible externally of the uterine cavity, and attaching the tandem proximal section to the thus-inserted tandem distal section. The method further includes intracavitarily placing one or more ovoid colpostats within the patient's vaginal cavity, this placing being in association with the tandem proximal section insertion. Thereafter, radiation treatment proceeds until a desired dosage is delivered, followed by removing the ovoid colpostat and the tandem proximal section from the patient, while retaining the tandem distal section within the uterus of the patient.

According to another embodiment, an intrauterine brachytherapy method includes providing intrauterine brachytherapy tandem and ovoid colpostat, inserting the tandem, assembled from a distal section and a proximal section of the tandem, within a patient's uterus. The method further includes intracavitarily placing one or more ovoid colpostats within the patient's vaginal cavity, this placing being in association with the tandem proximal section insertion. Thereafter, radiation treatment proceeds until a desired dosage is delivered, followed by removing the ovoid colpostat and the tandem proximal section from the patient, while retaining the tandem distal section within the uterus of the patient. When subsequent radiation treatment is scheduled, the tandem proximal section is inserted into the vaginal cavity and engaged with the tandem distal section, and the next treatment dose is administered.

In a further embodiment, a method and system having a brachytherapy tandem and ovoid colpostat further includes a component for shielding body portions not intended for radiation therapy. Shielding can be accomplished by one or more shield members and/or by one or more balloons. Shielding can achieve one or more functions, such as blocking or reducing radiation transmission through the shielding and/or spacing radiation sources away from undesired treatment locations and/or moving portions of the body cavity walls at locations where treatment is not desired away from radiation sources.

An additional embodiment concerns a system and method for brachytherapy tandem and ovoid colpostat radiation therapy where a radiation detector and a radiation data receiver are included. In a particular embodiment, the radiation detector is positioned on or in a balloon component, which balloon component is sized, shaped and positioned to impart separation and/or positioning with respect to the radiation source of the colpostat.

A further embodiment concerns a system and method for brachytherapy radiation therapy which includes a hyperthermia sub-system having a thermal delivery location generally adjacent to a radiation delivery location of the system and method. In a particular embodiment, the hyperthermia sub-system is generally adjacent to a radiation delivery location of a colpostat. In a further particular embodiment, the hyperthermia sub-system opens into the radiation delivery location of the colpostat.

Yet a further embodiment concerns a system and method for brachytherapy that includes, in combination, a hyperthermia sub-system and a radiation detector, both positioned in the close vicinity of the colpostat radiation delivery location. A radiation data receiver is located external of the body within which the brachytherapy is proceeding.

Another embodiment concerns a system and method for brachytherapy having an ovoid colpostat featuring adjustability, With this embodiment, a portion of the ovoid colpostat, such as a leg, is joined with the rest of the colpostat such that the leg can be changed into its orientation with the rest of the ovoid colpostat. Same, in embodiments as desired, can be combined with balloon shielding, radiation detecting and/or hyperthermia features, systems and/or methods.

In a further embodiment, a method and system having a brachytherapy tandem and ovoid colpostat further includes a component for shielding body portions not intended for radiation therapy. Shielding can be accomplished by one or more shield members and/or by one or more balloons. Shielding can achieve one or more functions, such as blocking or reducing radiation transmission through the shielding and/or spacing radiation sources away from undesired treatment locations and/or moving portions of the body cavity walls at locations where treatment is not desired away from radiation sources. In a further embodiment, the shielding function is combined with an ovoid colpostat having such shielding and/or balloon approach along with an ovoid colpostat adjustability to allow further tailoring of positioning of the shielding and/or balloon.

An additional embodiment concerns a system and method for brachytherapy tandem and ovoid colpostat radiation therapy where a radiation detector and a radiation data receiver are included. In a particular embodiment, the radiation detector is positioned on or in a balloon component, which balloon component is positioned on an ovoid colpostat that features adjustability to allow varied positioning of the radiation detector.

A further embodiment concerns a system and method for brachytherapy radiation therapy which includes a hyperthermia sub-system having a thermal delivery location generally adjacent to a radiation delivery location of the system and method. In a particular embodiment the hypothermia delivery site is variable by being associated with an adjustable ovoid. In a further embodiment, the hyperthermia sub-system is generally adjacent to a radiation delivery location of an adjustable ovoid colpostat. In a further particular embodiment, the hyperthermia sub-system opens into the radiation delivery location of an adjustable ovoid colpostat.

Yet a further embodiment concerns a system and method for brachytherapy that includes, in combination, a hyperthermia sub-system and a radiation detector, both positioned in the close vicinity of the colpostat radiation delivery location of an adjustable ovoid colpostat. A radiation data receiver is located external of the body within which the brachytherapy is proceeding.

BRIEF DESCRIPTION OF THE DRAWINGS

FIG. 1 is a side perspective view of an embodiment of an embodiment of the tandem and ovoid colpostats system;

FIG. 2 is a top perspective view of a distal portion of the system of FIG. 1 with the tandem shown in exploded view;

FIG. 3 is a top view similar to that system depicted in FIG. 1;

FIG. 4 is a side elevation view of a multi-section tandem showing a moderate degree of curvature along its distal portion;

FIG. 5 is a side elevation view of another multi-section tandem showing a degree of curvature along its distal portion more extensive than that of FIG. 4;

FIG. 6 is a side elevation view of a multi-section tandem assembly having a main member proximal section and a relatively short length detachable distal member;

FIG. 6A is a side lavational view of a detachable distal member for use with the main member proximal tandem section of FIG. 6, having a longer length;

FIG. 6B is a side elevational view of a detachable distal member for use with the main member proximal tandem section of FIG. 6, having an even longer length than in FIG. 6A;

FIG. 6C is a side elevational view of a detachable distal member for use with the main member proximal tandem section of FIG. 6, having a length longer than in FIG. 6B;

FIG. 7 is an enlarged detail view of an embodiment of the detachable distal portion, section or member of a tandem assembly;

FIG. 7A is a proximal end view of the detachable distal tandem portion of the FIG. 7 embodiment;

FIG. 8 is an exploded elevational view of a further embodiment of the multi-section tandem having the combination a proximal section sized, configured and made of material suitable for multiple-patient use and a detachable distal section sized, configured and made of material suitable for single-patient use, the tandem shown in a somewhat schematic representation of use in the body;

FIG. 8A is a view of the FIG. 8 embodiment as assembled;

FIG. 9 is a detailed view of an embodiment of the distal portion of an ovoid colpostat of the brachytherapy system, including shielding and a "real time" dosing monitor arrangement;

FIG. 10 is a detailed view of another embodiment of the distal portion of an ovoid of the brachytherapy system, also including shielding and "real time" dosing monitoring;

FIG. 12 is a perspective view of a brachytherapy system including a balloon component and dosing monitoring with diode-type arrangement;

FIG. 13 is a perspective view of another embodiment of a brachytherapy system including a balloon component and optional monitoring arrangement, positioned at a location different from that of FIG. 12;

FIG. 14A is a perspective view of yet another embodiment of a brachytherapy system including a balloon component positioned similarly to FIG. 14, illustrating dosing monitoring as well as a hyperthermia system;

FIG. 20 is a top view similar to the system depicted in FIG. 3 while including a balloon spanning the illustrated two ovoid colpostats;

FIG. 21 is a top view similar to FIG. 20 that includes a pillow-shaped balloon associated with each of the two illustrated ovoid colpostats;

FIG. 22 is a detailed view of another embodiment of the distal portion of an ovoid of a brachytherapy system, having shielding, electronic dose monitoring and ovoid adjustability;

FIG. 22A is the embodiment of FIG. 22 showing adjustable ovoid movement positioning;

FIG. 23A, FIG. 23B and FIG. 23C illustrate ovoid adjustability with a joint-type of arrangement;

FIG. 24 is a perspective view of a brachytherapy system including a plurality of balloon components and dosing monitoring;

FIG. 25 is a perspective view of another embodiment of a brachytherapy system including a balloon component and monitoring arrangement;

DESCRIPTION OF THE ILLUSTRATED EMBODIMENTS

Figure 11:
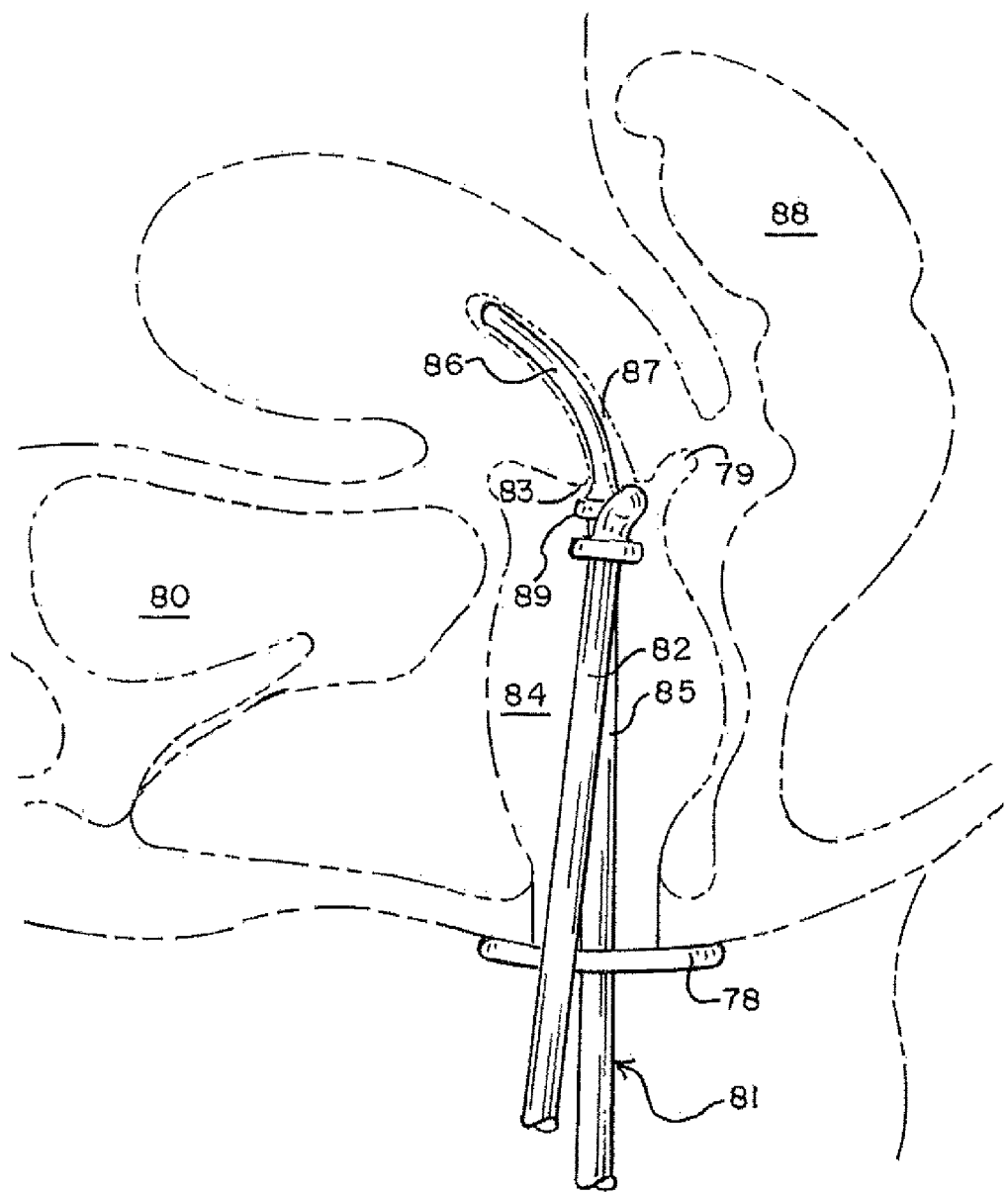
FIG. 11 is a somewhat schematic illustration of the distal portion of the brachytherapy system within a typical intrauterine environment.

The embodiments disclosed herein are exemplary only, and the subject matter described herein may be embodied in various forms. Therefore, specific details described herein are not to be interpreted as limiting the subject matter as defined in the accompanying claims.

FIG. 1, FIG. 2 and FIG. 3 illustrate an embodiment having a tandem generally designated at 31. In this embodiment, ovoids 32, 33 (also referred to as ovoid colpostats) are shown in a typical position flanking the tandem 31. In general, tandems can be a length on the order of 20 to 40 cm, depending upon the particular delivery system being used and patient being treated. It will be appreciated that the proximal end portion 34 of each ovoid colpostat attaches to a unit for supplying radioactive materials into the ovoid colpostat in order to direct the radioactive treatment material to the desired treatment site within the body of the patient. Details concerning loading of radioactive material into colpostats are not shown and are appreciated and understood by one of skill in this art.

The tandem 31 illustrated in this embodiment is sized and structured for intracavitary deployment, for example, intrauterine deployment. This illustrated tandem has a proximal section 35 and a distal section 36 that are detachably secured to each other. In FIG. 1, these sections are shown attached to each other, whereas in FIG. 2, they are detached from each other. Attachment is achieved according to any suitable approach or structure. For example, the distal end of the proximal section 35 and the proximal end of the distal section 36 contain mating components that are complementary with each other in that they attach to one another in a secure manner while they also detach from one another when desired and without excessive detachment force required. In this particular embodiment, the proximal section 35 includes a projecting component 37, which is sized, shaped and configured to be attachable and detachable to a receptor component 38 of the distal section 36 at its proximal end portion. These attachment components serve to assemble the tandem 31 into a cohesive unit that achieves function of prior art tandems, but with the additional functions described in this and other embodiments.

The proximal section 35 of tandem 31 is made of a durable material typically used for generally known tandems and brachytherapy equipment and procedures or otherwise determined to be suitable for tandems not having detachable features noted herein. Such a typical tandem is made of a metal, for example, stainless steel or other materials suitable for internal medical device multiple-time use, such as certain polymeric materials having the ability to maintain their desirable characteristics during harsh cleaning and sterilization conditions. Tandems tend to exhibit rigidity characteristics adequate to achieve known tandem functions. The typical tandem material is adequate to provide structural support and overall placement location for other components such as ovoid colpostats during a brachytherapy procedure. The proximal section 35 of the tandem 31 is most advantageously structured when made of a material that can withstand multiple cleanings, disinfectings and sterilization procedures. These are intended for multiple-time usage and typically for multiple patients.

By contrast, the distal end section 36 of tandem 31 is intended for single-patient brachytherapy use. This detachable distal section is sized and shaped for secure long-term implantation within a single patient during multiple radiation doses, as well as during interim time periods between radiation doses during a regimen of brachytherapy treatments. This detachable distal section can be made of a material intended for disposal after completion of a patient treatment regiment, and thus same need not be capable of being cleaned and sterilized multiple times. The basic concept of this detachable distal section 36 is that it remain in place and implanted within a patient during active brachytherapy treatment and during those down times or recovery times between brachytherapy treatments of a multiple-treatment brachytherapy plan or regimen.

Also illustrated in this embodiment is a placement pad 39 that can be useful in maintaining the proper location of the tandem before and during treatment. This can be a separate placement pad such as illustrated at 39 in FIG. 3 or can be a widened portion of the distal section 36. This latter approach can generally correspond to the receptor component 38 illustrated in FIG. 2.

Other versions of multi-component tandems are found in FIG. 4 and FIG. 5. Tandem 41 of FIG. 4 has a proximal section 45 and a detachable distal section 46 having an as-molded condition with a very gradual curve. Tandem 41a of FIG. 5 has a proximal section 45a and a detachable distal section 46a. Distal section 46a has a greater as-molded curvature than does distal section 46. It will be appreciated by one who has skill in the art that differently curved tandem components may be useful or needed due to physical variations from patient to patient.

The tandem, generally designated 41b in FIG. 6, includes a proximal section 45b and a detachable distal section 46b, the latter having a length on the order of 4 cm. This is an intracervical plastic applicator for uterine placement. FIG. 6A shows such an applicator that is depicted to represent a 6 cm length, while FIG. 6B illustrates an 8 cm length, and FIG. 6C illustrates a 10 cm length. These different lengths of detachable distal section tandem components are provided in order to accommodate different depths of the uterine cavity and cervix locations. A typical tandem 41b will have a length ranging between about 26 cm and about 34 cm.

FIG. 7 and FIG. 7A illustrate a distal section, generally designated 56, that is separable or detachable from a tandem proximal section such as 45b and 55. This embodiment includes a receptor component 58. When desired, the receptor component 58 can be radiopaque and/or metallic or made of metal. In an arrangement such as this, a projecting component, such as 59 or component 37 illustrated in FIG. 1, will be received within passageway 51. FIG. 7 and FIG. 7A indicate the passageway can include a stepped-down portion 52 to accommodate a stepped-down portion 57 of the projecting component 59 of the distal end portion of the proximal section 55 of the tandem.

When desired, the passageway and (whether in the tandem distal or proximal section of any of the embodiments), the corresponding receptor component can include interfering elements with complementary elements provided on the extending member of the proximal or distal section of that embodiment. These types of features help to prevent unintended detachment between the proximal and distal sections of the tandem assembly. Examples of complementary interfering paired elements are threads, indents and detents, snap rings and annular elements.

For example, the distal end portion of the proximal section 55 has a male element 59 with threads and the stepped-down end to matingly engage with threads in the passageway 51 and the stepped-down portion thereof. In addition, when desired, one or more projections or bumps, such as pins 54 can be included at the distal end portion of the tandem proximal section 55, which may be radiopaque, these being sized and shaped to be matingly accommodated by corresponding hole or holes 53. Alternatively, pin or pins can be on the proximal end of the distal tandem section, which may be radiopaque, and receptor hole or holes can be in the distal end portion of the proximal tandem section. Radiopaque materials are generally known in the art and can be metallic or combinations or coatings including radiopaque materials FIGS. 8 and 8A show a further embodiment of a detachable tandem assembly 61, including a proximal section 65 and a distal section 66. Proximal section 65 extends proximally outside of the body and into the vaginal cavity 62. When implanted as shown in FIG. 8 and FIG. 8A, the distal section 66 is within the uterus 63. In this illustrated embodiment, the distal section 66 includes a placement pad 69 that, when implanted, is in the general area of the cervix of the patient. With this embodiment, the receptor component 68 is provided on the proximal section 65 and a complementary extending element 64 at the proximal end portion of the distal section 66. The receptor component 68 may be radiopaque, or metallic, or made of metal. In this embodiment, the extending element 64 enters into and matingly engages with the receptor component 68. Suitable interfering elements can be provided on either or both of the extending element 64 or receptor component 68 as previously generally discussed.

FIG. 9 provides further details of the ovoid component, generally designated 32, as an example of an ovoid colpostat that can be provided in the association system illustrated in FIG. 1, FIG. 2 and FIG. 3. The ovoid colpostat 33 shown in FIG. 9 includes proximal end portion 34 by which radioactive material is added thereinto by communication with dispensing equipment (not shown) familiar to one of skill in this art. In a typical treatment protocol, the radioactive material is delivered to the internal distal delivery location 71. Often during treatment, this distal delivery location 71 is for treating a diseased cervix or fornix, for example. Depending upon the treatment plan in place, it can be important to include a shielding element, such as element 72. Typically a shield can be made of lead, tungsten or other radiation-blocking material. Shielding element 72 also can provide a stand-off function to increase spacing between the internal distal delivery location 71 and a portion of the body that is not to be subjected to treatment. Examples of such body portions are the bladder and rectum. The shield 72 is illustrated positioned at the tip of the ovoid colpostat 32. In the illustrated position the shield 72 can help protect the rectum, for example.

Also illustrated in FIG. 9 is a balloon arrangement that can be implemented for patient protective reasons. A balloon 75 is shown positioned near the ovoid primary bend. This balloon typically can be useful in pushing away rectum tissue, for example, when it is inflated, only part inflation shown. Balloon inflation shown is carried out by passing saline solution or gas such as air or nitrogen through a conduit 76a to the balloon 75 from a source of inflation fluid (not shown).

In this embodiment, a detector 76 is on or associated with the balloon 75 in order to detect and measure in vivo dosing and radiation. If desired, "real time" detection, measurement, observation and/or recordal of radiation data can proceed. Typically the detector is placed in an area distal to a shield or in or on a balloon near such a location. Transmission of the detector data can be by a wireless system, or a transmission wire or lead 77 can be used, a data receptor 77a being shown. A typical detector is a microdiode.

FIG. 10 shows another ovoid component, generally designated 33. This ovoid colpostat has an internal distal delivery location 73. Similar to ovoid colpostat 32, this ovoid colpostat can include a shielding element 74 provided for essentially the same function. A second shielding element 75a is included in this embodiment, being positioned near the primary bend of this ovoid. A balloon 75a is shown in this same general location and has a detector 76 and conduit 76a similar to FIG. 9.

Balloon 75a can be positioned for pushing away bladder tissue in this embodiment. Shield 74a can be considered to sit on top of the colpostat to shield the bladder. Usually, these shielding elements 72, 74, 74a are medial and face each other when in use. Shielding material of the embodiments illustrated in FIG. 9 and FIG. 10 can be made of lead, tungsten, stainless steel, other metal, or a metal impregnated polymer, such as a lead-impregnated polymer.

While ovoid components 32 and 33 are illustrated in FIG. 9 and FIG. 10 to be of substantially the same size and shape, it will be appreciated that these ovoid components can vary from one to another in size, shape and intended function. For example, different ovoid components may be beneficial when intended for asymetric tumor treatment or similar non-uniform target. Some ovoid components may be shaped and sized to dose regional (obturator) lymph nodes, perhaps involving "isodore curves", for example. Ovoid components also can include so-called caps, typically as an added component to an ovoid colpostat as a buffer or protector to reduce the chance of damage caused by a relatively thin colpostat.

Another embodiment of a tandem and ovoid combination is illustrated in FIG. 11. An assembled tandem, generally designated 81, is shown associated with an ovoid colpostat 82. The tandem includes a proximal section 85 and a distal section 86. The distal section may include a placement pad 89 in the area of the fornix 79 and/or the cervix 83, typically positioned within the distal volume of the vaginal cavity 84 and closely spaced outside of the uterus 87. Bladder 80 and rectum 88 also are shown in this drawing. In this particular embodiment, the assembly includes a block 78 that can be secured to define a given length of the device between the cervix and the opening of the vaginal cavity. Alternatively, when the block 78 or similar component is provided, same can be slidable along the device so as to adjust this distance with a view toward maintaining a desired length, such as between the cervix and the opening of the vaginal cavity or between the tandem and ovoids.

Embodiments can include one or more balloon devices. FIG. 12 shows a tandem, generally designated 61, onto which is secured by an assembly unit 92 ovoid colpostats 32 and 33. Assembly unit 92 can take the form of known brackets, staples, sleeves, or mobile blocks of tandem and ovoid assemblies. With the tandem properly positioned, any necessary adjustments are made at the assembly unit 92 so that each ovoid component 32, 33 is positioned properly for treatment of a desired area, such as at the cervix or fornix area. The assembly unit then secures the ovoids with respect to the tandem as treatment progresses.

The balloon, generally designated as 91, is shown in FIG. 12 positioned so as to space one or more of the ovoids away from the vaginal wall to assist in minimizing undesired radiation exposure. The illustrated balloon includes a shaft 93 having an inflatable balloon member 94 spaced therealong, such as along a distal portion of the shaft. The shaft 93 includes a lumen that is secured to a suitable device (not shown) of known construction and features that provide inflation fluid, typically saline liquid or gas such as air or nitrogen, into the lumen 95 and distally therethrough until exiting through an opening therein into the balloon member 94. Such passage of inflation material inflates the balloon member, while removal thereof deflates the balloon member in a manner appreciated in the art.

The balloon of this or other embodiments may have radiopaque marking or may be radiopaque in whole or in part. Alternatively or additionally, the balloons of the various embodiments may include microdiodes attached or other devices or systems to provide "real-time" in vivo measuring of radiation. To this end a detector 76 is shown while transmission associated with same can be wireless connection lead or wire 77 is shown leading to data receptor 77a in FIG. 12 and FIG. 13. In FIG. 13, two detectors 76b and 76c are shown. These detect radiation at different locations and can have a common lead or separate leads to the data receptor.

Figure 14:
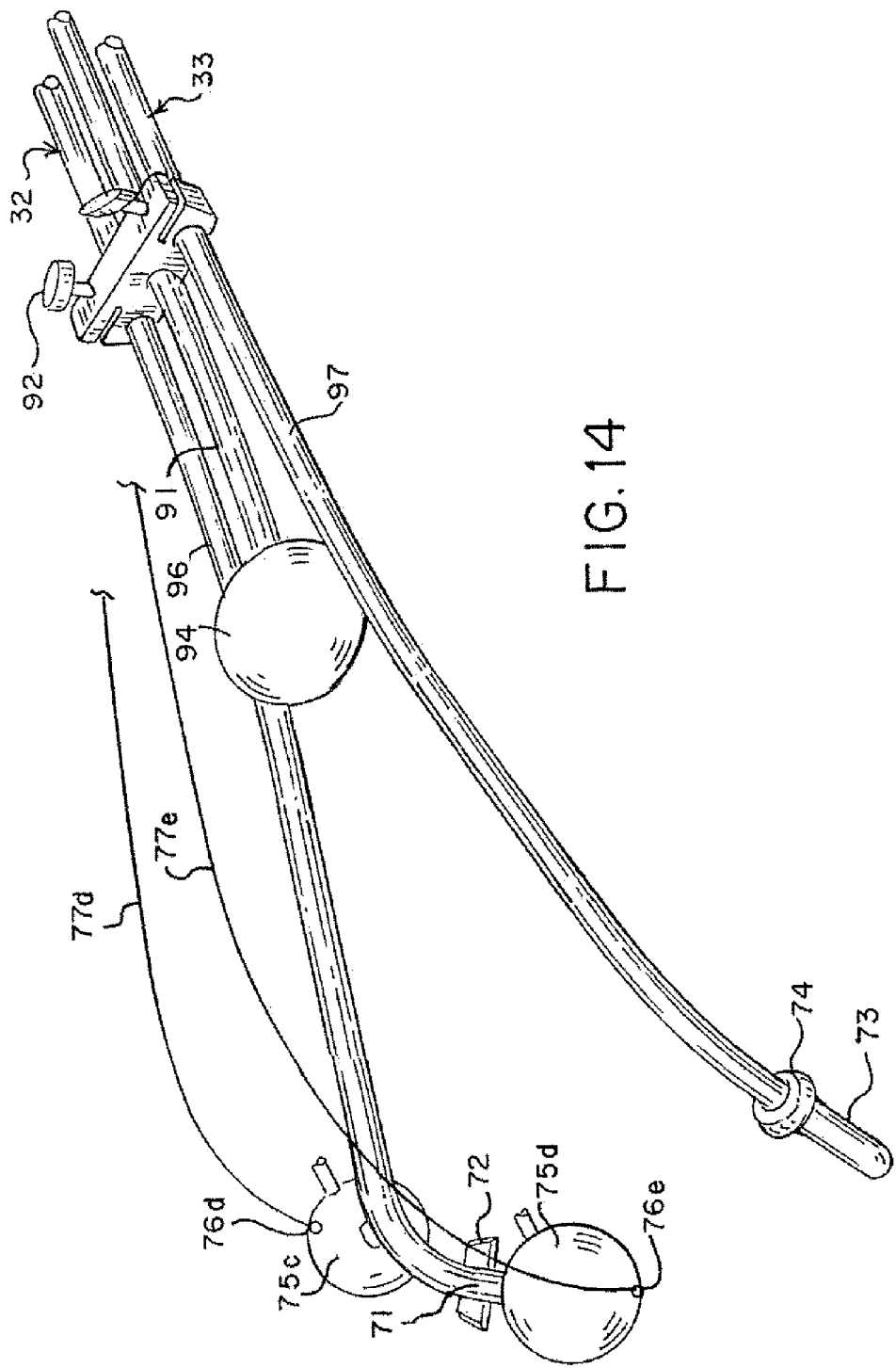
FIG. 14 is a perspective view of a further embodiment of a brachytherapy system including a balloon component positioned at a location different from either FIG. 12 or FIG. 13 and useful for an ovoid separation function, also illustrating placement of "real time" dosing monitoring.

FIG. 14 illustrates an embodiment along the lines of those of FIG. 12 and FIG. 13. Here, the balloon 91 is positioned between ovoids 32 and 33, in this case along a length of each ovoid that is spaced proximally from its respective internal distal delivery location 71, 73. More specifically, the balloon member 94 is positioned at intermediate bend 96, 97 at the respective ovoids 32, 33, more specifically along the shaft of each such ovoid. With this FIG. 14 embodiment, the balloon member 94 inflates while between these intermediate locations 96, 97, preferably at their respective bend locations as illustrated in FIG. 14. As inflation progresses, positioning between the ovoids is adjusted and secured during treatment. As desired, added inflation can open the spacing between the ovoid colpostat delivery locations 71, 73. Maintenance of the balloon pressure maintains this spacing during brachytherapy to assist in proper location of the treatment radiation. FIG. 14 further illustrates assembly unit 92 which maintains positioning of the ovoids with respect to each other at a location proximal of the intermediate locations. This is a component of the separation and positioning function of the balloon in this embodiment.

Additional balloons 75c and 75d are shown as alternate embodiments. Each has a detector 76d, 76e, respectively, and leads 77d, 77e, respectively are illustrated. It will be appreciated that this particular arrangement allows the user to detect and measure radiation at separate locations in the general vicinity of this particular ovoid. An arrangement along these lines can be provided with respect to the other ovoid. Also shown (in FIG. 14A) as an alternate embodiment is a detector 76f and lead 77f positioned internally of the balloon 91 including either or both of its balloon member 94 and its tube joining balloon member 94 to the fluid supply (not shown). Alternately, detector and/or lead are positioned within the wall of the tube and/or of the balloon member, rather than outside or inside such walls.

FIG. 14A shows modification of the FIG. 14 system that incorporates a hyperthermia system by which heat can be applied to the cancerous area simultaneously with the radiation treatment or if desired in close association in time and location with the radiation treatment imparted by the colpostat means. More specifically, the hyperthermia system includes delivery tubes 143, 144 that extend between a target location and a hyperthermia fluid source (not shown) of generally known characteristics and structure, such hyperthermia fluid source being outside of the body. In this illustrative embodiment, each hyperthermia delivery tube 143, 144 is secured by the assembly unit 92. As shown, this securement can be achieved, for example, by having the tube pass through an opening 146 such as a slotted keyway through the assembly unit. In this illustration, such keyway opening is adjacent to the location at which the ovoid colpostat 32, 33 is secured by the assembly unit 92.

In this illustrative embodiment, the target location is in the vicinity of the location at which the colpostat delivers the radiation, which can be low dose radiation, for example. Thus, delivery tube 143 is positioned generally adjacent ovoid delivery location 71 of an ovoid such as colpostat 32. Hyperthermia delivery tube 144 is shown positioned in direct contact with a widened location 145 at the ovoid delivery location 73 in the other illustrated ovoid colpostat 33 illustrated in FIG. 14A. Tube 144 applies heat in this colpostat area and generally adjacent to the radiation delivery site. If desired, the tube 144 can open into the widened location 145 to thereby provide flow of the hyperthermia treatment fluid into this location 145, whereby an integral hyperthermia treatment administration site is positioned at a specific location that is substantially at the radiation delivery site.

When all of the features and structures shown in FIG. 14A are implemented in a single system, the advantages of hyperthermia are combined with radiation treatment whereby the target tissue is raised in temperature during, or close in time before or after, radiation treatment, which can enhance the effectiveness of the radiation treatment. In addition, the microdiodes or the like, as described elsewhere herein, provide "real time" in vivo detection and measurement of the radiation delivered, which can assist in tailoring a radiation regimen for the particular patient. Moreover, this detection and measurement is carried out at, or in very close proximity to the, location of the radiation treatment and, when desired, also of the hyperthermia treatment, with the objective of providing an unusually efficient and effective combination of patient treatment features.

Figure 15:
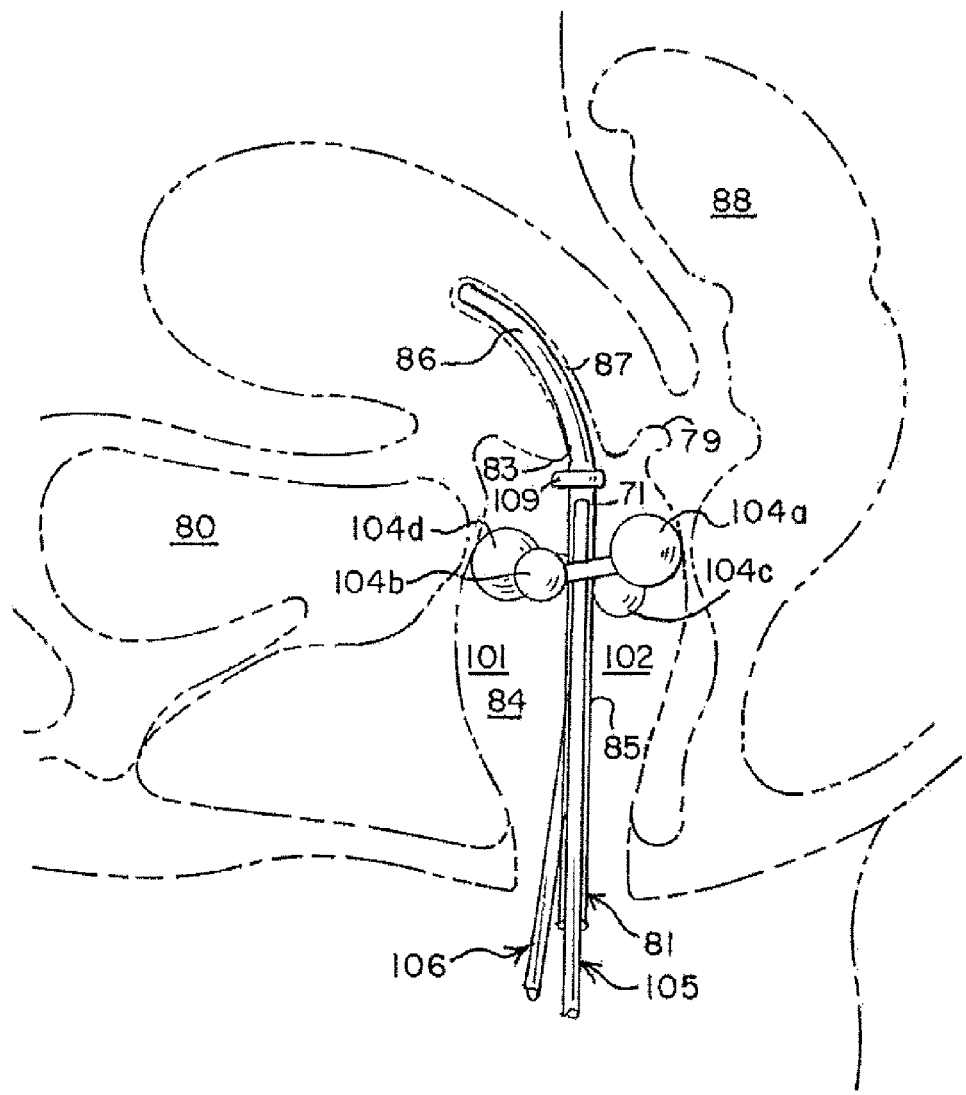
FIG. 15 is a somewhat schematic side-view illustration of a brachytherapy system including balloon members, showing multiple balloon members (two being visible) at functional locations during an intrauterine procedure and positioned for providing a stand-off function during an intrauterine procedure.

The vaginal cavity 84 of FIG. 15 is shown as having an anterior region 101 and a posterior region 102, and FIG. 15 can be considered a first side view illustrating anterior and posterior balloon placement capable of being accomplished by the treatment method. This embodiment includes tandem 81 having proximal section 85 and distal section 86. Also included is placement pad 109, which in this embodiment also functions in the assembly structure by which the proximal and distal sections are assembled and selectively disassembled, when that feature is included in this embodiment. Two ovoid colpostats, generally designated at 105 and 106, are shown in association with the tandem 81. Each such ovoid includes two balloon members. Balloon members can be mounted onto, added to or associated with an ovoid colpostat cap 77 (FIG. 17).

As illustrated in FIG. 15, ovoid 105 has opposing balloons 104a and 104b, while ovoid 106 has opposing balloons 104c and 104d. Both the anterior and posterior regions of the vaginal cavity 84 are moved farther away from the radiation oncology treatment site, such as at the cervix 83. This successfully opens the vaginal cavity at an interior location that is relatively closely spaced from the cervix or other treatment target site. It will be appreciated that, by this approach, the balloons 104b and 104d move the anterior region 101 away from radiation emitted by the ovoid colpostats such as distal delivery location 71 illustrated in FIG. 15. In much the same manner, the balloons 104a, 104c move the posterior region 102 away from the radiation source or sources. It will be appreciated that, as the balloons inflate when within the vaginal cavity, this safety-driven opening of or movement away from radiation sources is accomplished.

Figure 16:
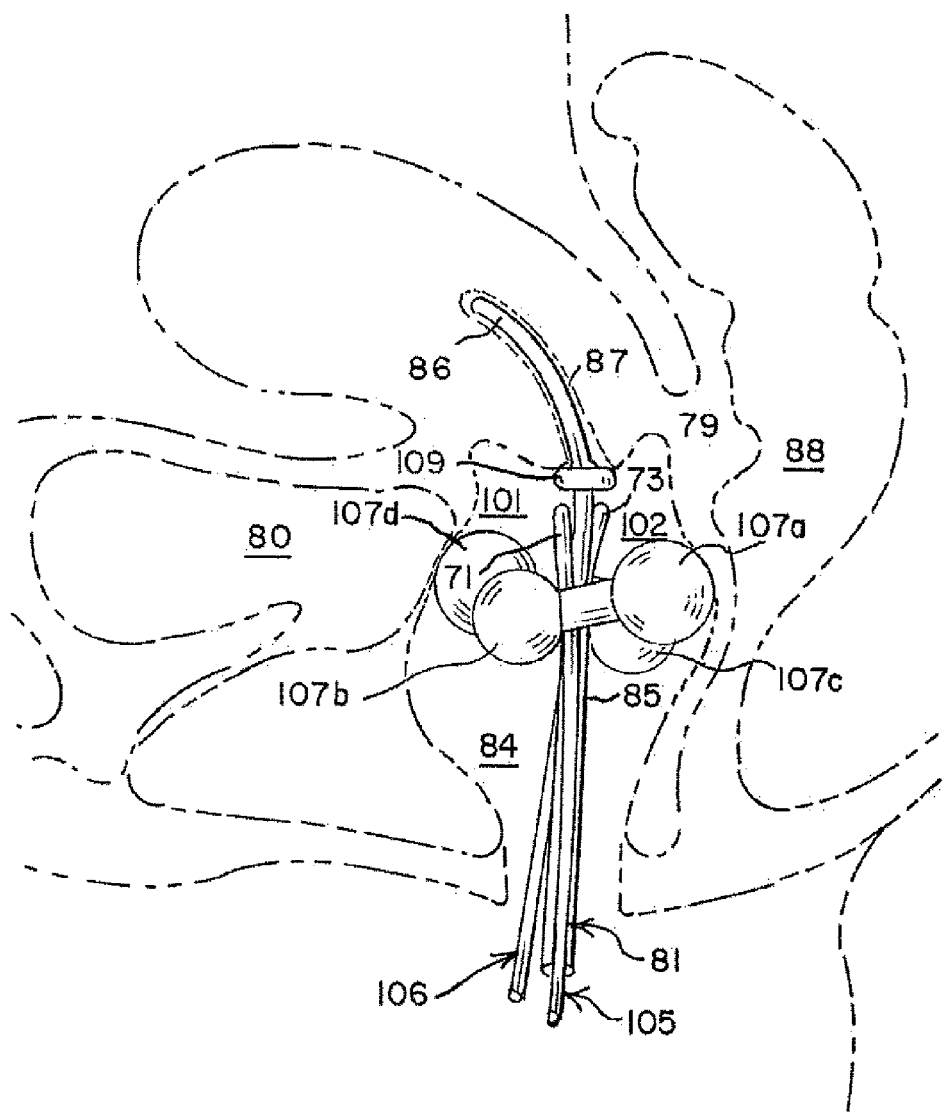
FIG. 16 is a somewhat schematic side-view illustration of a brachytherapy system including balloon members of FIG. 15, showing the balloon members providing a stand-off function during an intrauterine procedure.

FIG. 16 is a second side view similar to FIG. 15. In this arrangement, the balloons 104a, 104b, 104c and 104d and the associated supportive structure for them respectively move the anterior region 101 to such an extent that the bladder wall itself is moved away from the radiation source. This also illustrates the balloons moving the posterior wall to such a degree that a portion of the wall of the rectum 88 is moved away from the radiation source. The balloons 107a, 107b, 107c and 107d that are illustrated in FIG. 16 are expanded to a greater extent than in FIG. 15, with the result that further vaginal opening is achieved while also moving the walls of the bladder 80 and rectum 88 that are closest to the radiation source farther away from the radiation source emanating from the distal delivery locations 71 and 73.

Figure 17:
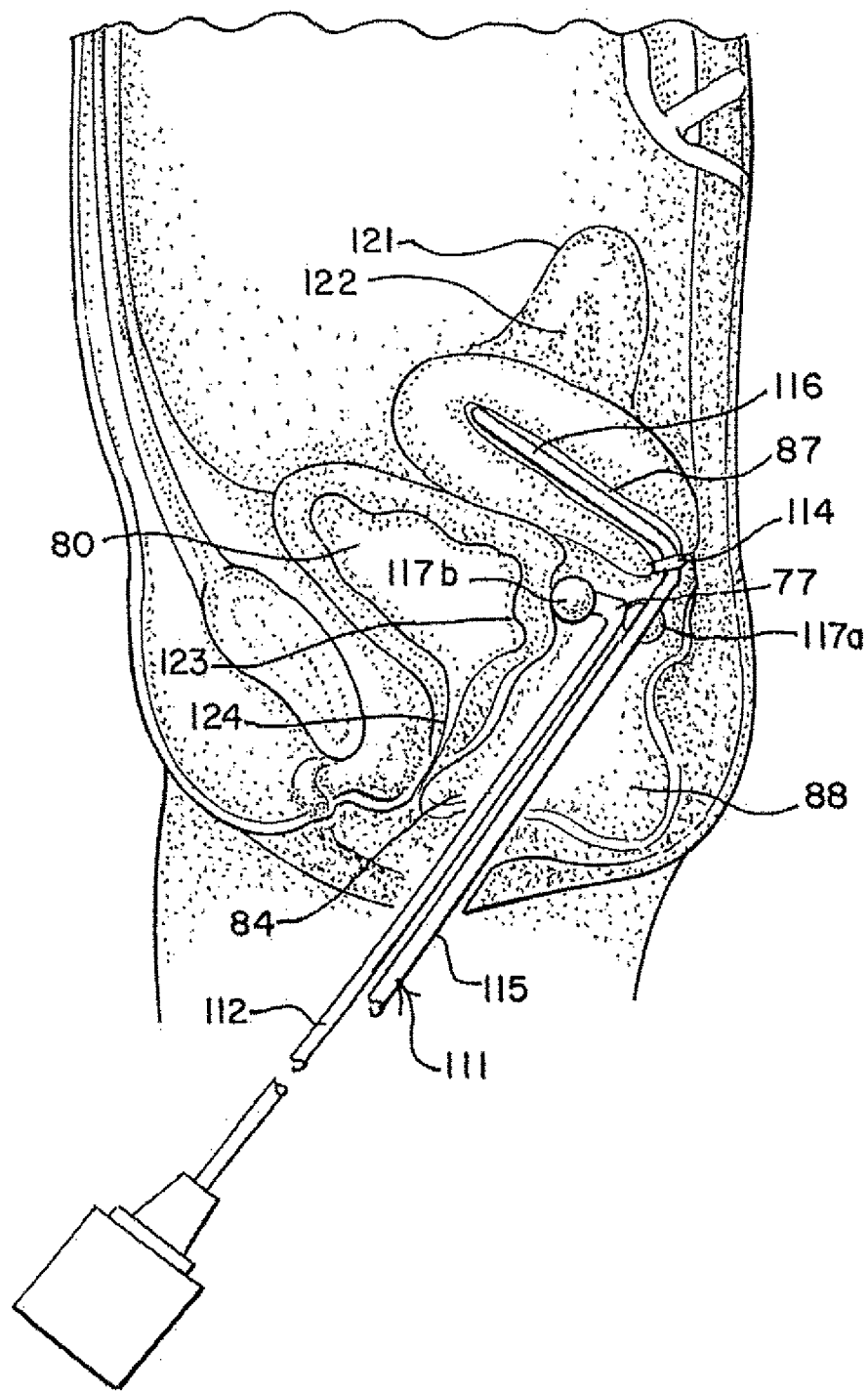
FIG. 17 is a further somewhat schematic side-view illustration of a tandem and of an ovoid colpostat with balloon component secured at a distal end portion of the colpostat.

A further embodiment is shown in FIG. 17. A tandem, generally designated 111, is provided along with an ovoid colpostat 112 which receives radiation pellets or the like from a radiation source 113. The tandem includes a proximal section 115 which extends from outside of the body and vaginal cavity 84, and is releasably connected to the distal section 116 of the tandem. A combination connector and placement pad 114 is at the intersection between the proximal and distal sections. The distal section 116 is shown placed within the uterine cavity, with its distal portion extending just outside of the uterine cavity as shown. In addition to the bladder 80 and rectum 88, the following also are shown in this drawing: fallopian tube 121, ovary 122, pubic bone 123 and urethra 124. The illustrated ovoid colpostat 112 includes balloons 117a and 117b. When inflated, these balloons are useful in moving body components away from the treatment portions of the ovoid colpostat, allowing the colpostat to deliver radiation to the treatment site while increasing the distance between the treatment site and body locations that are not to be subjected to the radiation oncology treatment. It is contemplated that a second ovoid colpostat (not shown in FIG. 17) can be included. The second ovoid colpostat can include a balloon or balloons depending upon the particular needs of the treatment.

Figure 18:
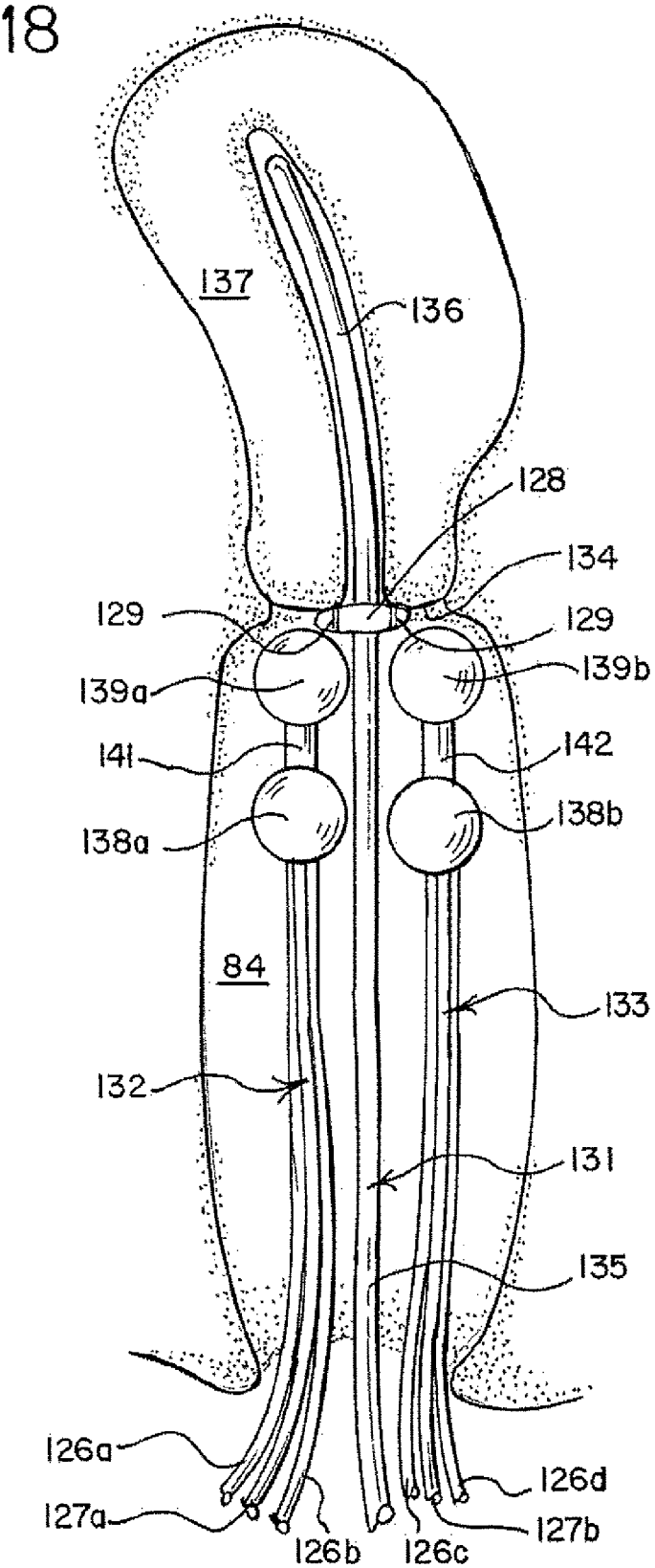
FIG. 18 is a schematic top-view illustration of a tandem and dual ovoid colpostats system having four deployable balloons visible.

FIG. 18 is a schematic view in the nature of a perspective top view of an inserted system of tandem and ovoid colpostats. Tandem, generally designated 131, is flanked to the left and to the right (as oriented in this view) by ovoid colpostats 132 and 133, respectively. It will be understood that the distal section 136 of the tandem extends into the uterine cavity 137, and the proximal section 135 of the tandem, as well as the ovoid colpostats 132, 133, extend well within and outside of the vaginal cavity and in the area of or proximal to the cervix 134. In this illustrated orientation, the posterior left balloon 138a and the posterior right balloon 138b engage the uterine wall and expand same so as to push on the rectum of the patient and thus move same away from the colpostat and the radiation emission. Anterior left balloon 139a and anterior right balloon 139b inflate to engage and move a portion of the vaginal wall into the normal bladder space, thereby moving the bladder wall at the general area of these balloons away from the colpostat and its radiation source.

In this particular embodiment, separate pathways are provided for filling individual balloons. Pathway 126a fills or otherwise controls size of posterior left balloon 138a. Pathway 126b fills or otherwise controls anterior left balloon 139a. Lumen 127a attaches to a radiation source such as an HDR source as discussed elsewhere herein. Lumen 127b connects ovoid 137 to a radiation source in a similar manner. Pathway 126c provides inflation liquid or gas to anterior right balloon 139b, while pathway 126d provides gas or liquid passage into the posterior right balloon 138b. When desired, multiple such lumens can be controlled by the same source of gas or liquid. For example, lumens 126a and 126c can be connected to the same source channel so that both anterior balloons 139a and 139b inflate and deflate in general unison. Similarly, pathways 126b and 126d can be controlled by the same source of gas or liquid in order to generally simultaneously control inflation and deflation of posterior balloons 138a, 138b.

Figure 19:
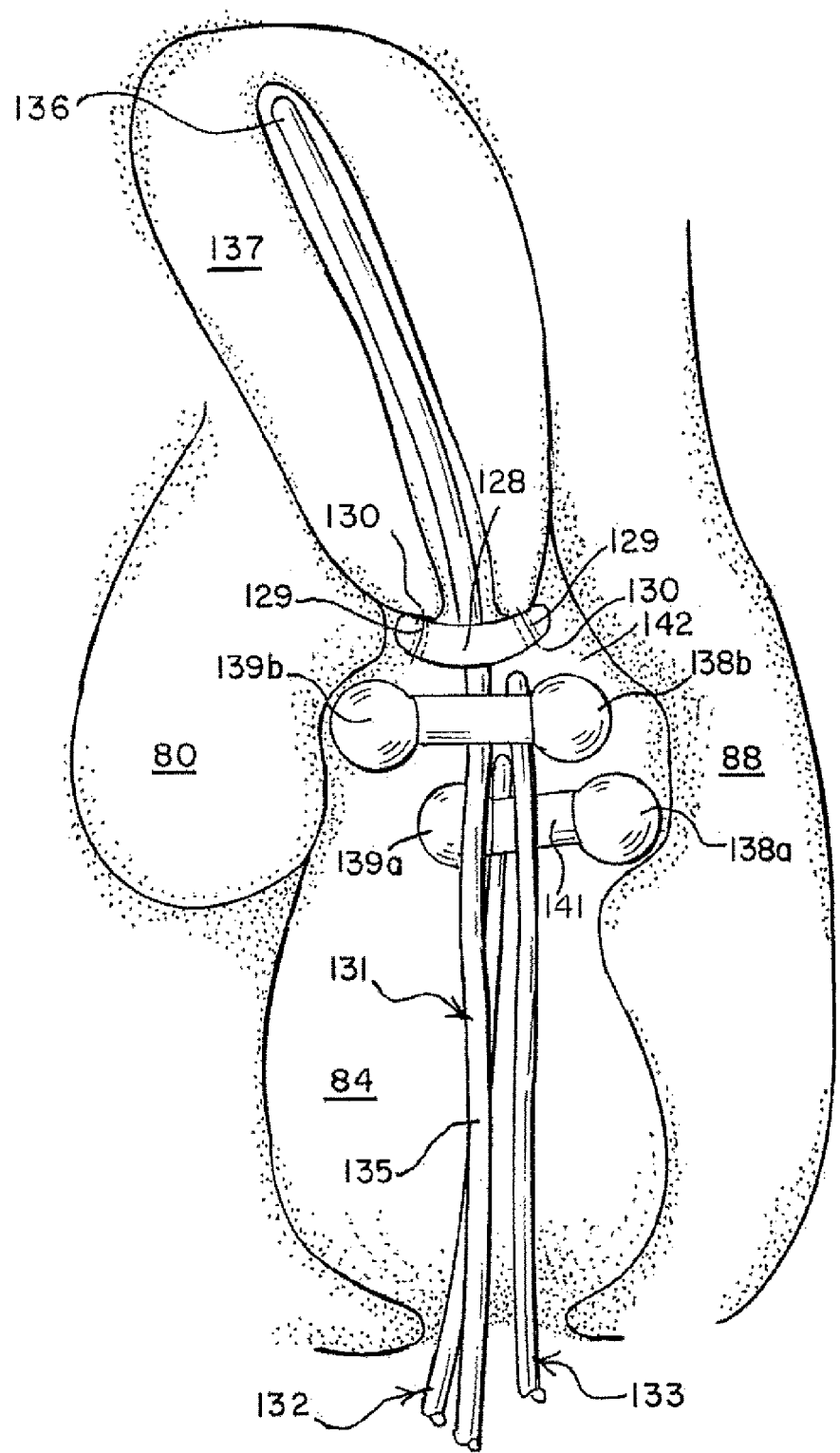
FIG. 19 is a schematic sagittal-view illustration of a tandem and dual ovoid colpostats system having four deployable balloons visible.

In FIG. 18 and FIG. 19, each balloon is shown mounted to its ovoid by way of a transverse extender that spaces the balloon apart from the ovoid tube in a direction toward a vaginal wall, typically either anteriorly or posteriorly. Such transverse extender includes or supports the lumen through which the balloon is inflated and deflated, which lumen can be interior of the transverse extender to enhance compactness and integrity of the ovoid system. Thus, in these drawings, transverse extender 141 mounts balloon 138a and 139a, while transverse extender 142 mounts balloon 138b and 139b. These extenders, in use, facilitate placement of the balloon so as to assist same in engaging the vaginal cavity wall, in moving such wall outwardly so as to cause further outward movement of a body component that is not a radiation target, for example, the bladder and/or rectum, which is illustrated in these drawings.

A cap 128 is illustrated at a location overlying the cervix 134. This can take the form of a polymeric ring or "donut" that is part of or secured to the distal section 136 of the tandem 131. This doughnut-like component is sized and shaped so as to be secured, such as by suturing, to the cervix or cervical area, for example. When desired, one or more holes 129 are included in the cap or ring 128 to facilitate attachment. It will be appreciated that such attachment will be maintained in between oncology treatments and when the ovoids and the proximal section 135 of the tandem are removed from the body.

Another view of an embodiment generally following that of FIG. 18 is somewhat schematically illustrated in FIG. 19 as a sagittal view. In this view, the posterior left balloon 138a and the posterior right balloon 138b are shown against the vaginal cavity wall pushing same outwardly into and with a portion of the wall of the rectum 88. Also shown are the left anterior balloon 139a and the right anterior balloon 139b engaging and moving the uterine cavity wall into and with a portion of the wall of the bladder 88. With the arrangement shown in FIG. 19, portions of the bladder and of the rectum that are in the vicinity of the radiation treatment from the ovoid colpostats 132, 133, thereby minimizing the risk of unintentional radiation exposure to the bladder and rectum. A cap or ring 128 is shown in this view sutured to the body of the patient with sutures 130 passing through holes 129. This suturing facilitates retention of a distal section 136 of tandem 131 during patient recovery periods between active treatment sessions for that particular patient.

FIG. 20 illustrates an embodiment having the tandem 31 and ovoids 32, 33 of FIG. 3 where the proximal end portion 34 of each ovoid colpostat attaches to a unit for supplying radioactive materials into the ovoid colpostat in order to direct the radioactive treatment material to the desired treatment site within the body of the patient and the tandem has a proximal section 35 and a distal section 36 that are detachably secured to each other. A balloon member 151 is shown spanning both ovoid colpostats 32, 33 while being above (as viewed in this drawing) the tandem 31. This is a wide-surfaced balloon member that achieves more uniform pushing away of the tissue protected by the balloon member when compared to smaller surface area balloon members that can have a tendency to burrow into the tissue whereby the balloon becomes enveloped (partially or fully) into the tissue, reducing the balloon's ability to push away tissue.

Balloon 151 can be secured to the ovoids in this illustrated embodiment and the other embodiments hereof permanently in which event same must be sterilized between uses and while secured to the ovoid. Alternatively, balloon 151 can be removably attached to each ovoid or tandem, in which event the balloon can be provided in sterile packaged condition, attached to the ovoids, used once and disposed of properly.

FIG. 21 modifies the arrangement of FIG. 20, including multiple balloon members 152, 153 attached to the respective ovoid colpostats. Each balloon member can be permanently or removably attached to its ovoid colpostat for multiple-time uses or single-time use.

FIG. 22 shows another ovoid component, generally designated 33a. Similar to FIG. 10, this ovoid colpostat has an internal distal delivery location 73. Shielding element 74 and a second shielding element 75a, a balloon 75a, a detector 76 and a conduit 76a are shown. This ovoid component 33a has a bendable section 152 at a turn of the ovoid. Bendable section does not interfere with movement of radioactive material through the colpostat at the bend, typically featuring a non-obstructed tube for radioactive material delivery. This illustrated version has corrugation components that allow for movement or bending with "infinite" variability while maintaining the positioning selected by the user in response to engagement forces typically encountered as the device is moved into the body cavity and encounters body tissue. Thus, the corrugations have enough stiffness to withstand forces encountered when the user inserts the particularly assembled ovoid colpostat into the body cavity and throughout treatment.

FIG. 23A, FIG. 23B and FIG. 23C show an alternate embodiment of an ovoid colpostat 33b having a bendable section 153. Rather than corrugations, a joint assembly is positioned at the bend. Joint assembly can take a variety of forms while not interfering with passage of radioactive material through the colpostat. For example, leg 154 and body 155 of the colpostat 33b can be separate components with opposing ends that engage each other with a shallow pin joining them. It will be appreciated that the joint can include multiple interference stops (not shown) to facilitate securing the bend at, for example, approximately 135° of FIG. 23A, 120° of FIG. 23B or 90° of FIG. 23C.

FIG. 24 shows a tandem and ovoid colpostat assembly following those of FIG. 12, but with large surface area balloon members. A first balloon, generally designated as 91a, is shown in FIG. 24 positioned so as to space both of the ovoids away from the vaginal wall to assist in minimizing undesired radiation exposure. The illustrated balloon includes a shaft 93 shown as bifurcated into first branch 154 and a second branch 155. Branch 154 has an inflatable first wide-area balloon member 94a spaced therealong, while branch 155 has a second wide-area balloon member 156. The shaft 93a includes a lumen that is secured to a suitable device (not shown) of known construction and features that provide inflation fluid, typically saline liquid or gas such as air or nitrogen, into the lumen 95 and distally therethrough until exiting through an opening therein into the respective balloon members 94a and 156. In this illustrated arrangement, balloon 94a provides protection at the ovoid bends while balloon 156 provided protection at the distal colpostat delivery sites.

Each branch 154, 155 can be independently operated by providing the lumen with dual longitudinal passageways, opening into the respective branches 154, 155. Greater than two lumen passageways can be provided to selectively inflate and deflate respective multiple balloon members in this and other embodiments hereof.

The balloon or balloons of this or other embodiments may have radiopaque marking or may be radiopaque in whole or in part. Alternatively or additionally, the balloons of the various embodiments may include microdiodes attached or other devices or systems to provide "real-time" in vivo measuring of radiation. To this end a detector 76 is shown in FIG. 24. While transmission associated with a detector or detectors can be a wireless connection, lead or wire 77 is shown leading to data receptor 77a in FIG. 24 and FIG. 25. In FIG. 25, two detectors 76b and 76c are shown on one of the balloon members. These detect radiation at different locations and can have a common lead (allowing for separate data paths) or separate leads to the data receptor. A detector or detectors can be included at 76g, 76h, 76i, 76j, 76k and 76l of FIGS. 24 and 25, each being shown as a wireless detector.

Figure 26:
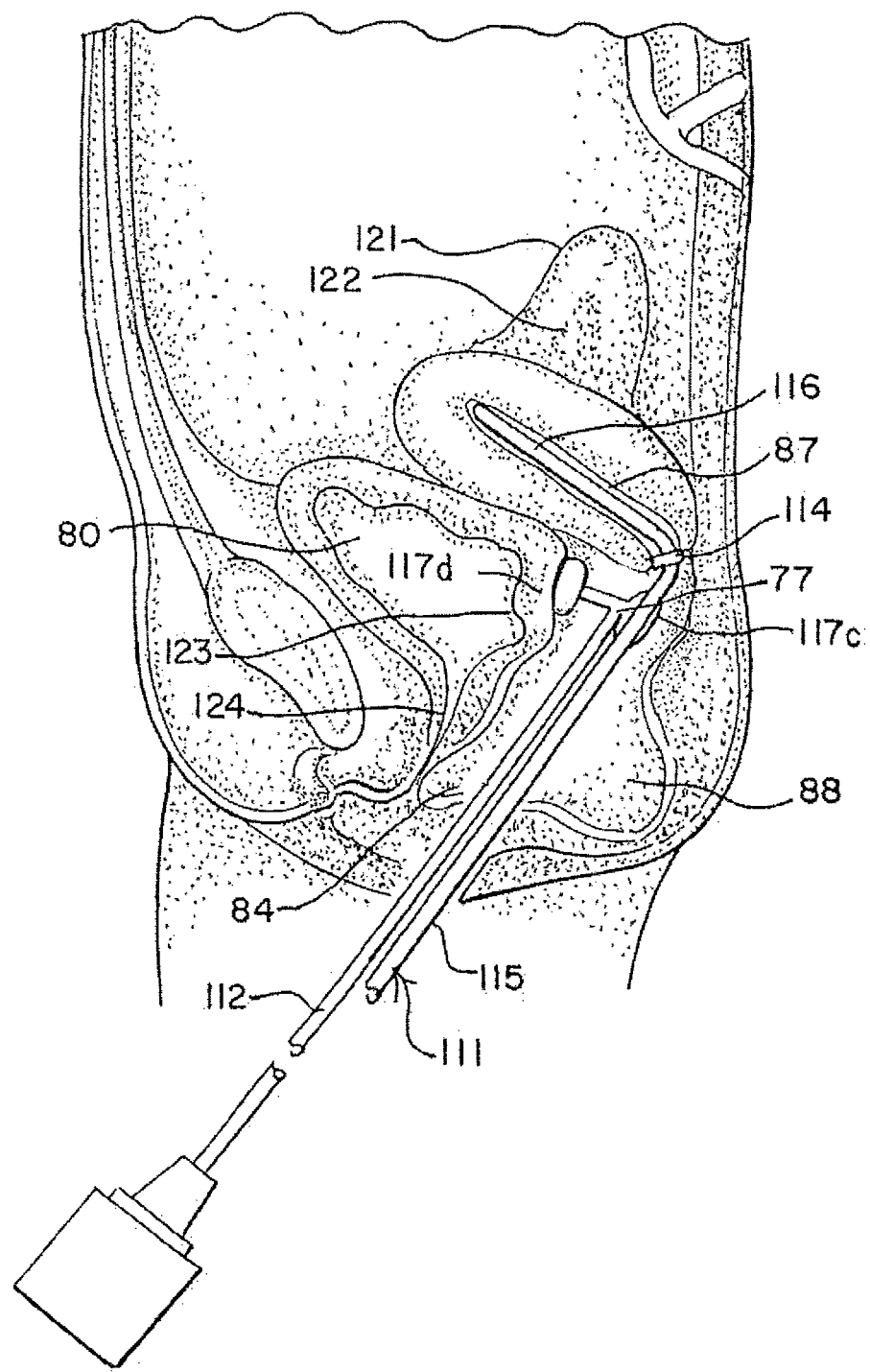
FIG. 26 is a further somewhat schematic side-view illustration of a tandem and ovoid colpostat with a wide surface area balloon at the distal end of the colpostat.

A further embodiment is shown in FIG. 26. Similar to FIG. 17, shown is a tandem 111, and an ovoid colpostat 112 which receives radiation pellets or the like from a radiation source 113. The tandem includes a proximal section 115 which extends from outside of the body and vaginal cavity 84, and is releasably connected to the distal section 116 of the tandem. A combination connector and placement pad 114 is at the intersection between the proximal and distal sections. The distal section 116 is shown placed within the uterine cavity, with its distal portion extending just outside of the uterine cavity as shown. Engagement with walls of the bladder 80 and rectum 88 are shown in this drawing. The illustrated ovoid colpostat 112 includes wide-surface balloons 117c and 117d. When inflated, these balloons are useful in moving body components away from the treatment portions of the ovoid colpostat, allowing the colpostat to deliver radiation to the treatment site while increasing the distance between the treatment site and body locations that are not to be subjected to the radiation oncology treatment. It is contemplated that a second ovoid colpostat (not shown in FIG. 26) can be included. The second ovoid colpostat can include a balloon or balloons depending upon the particular needs of the treatment.

Figure 27:
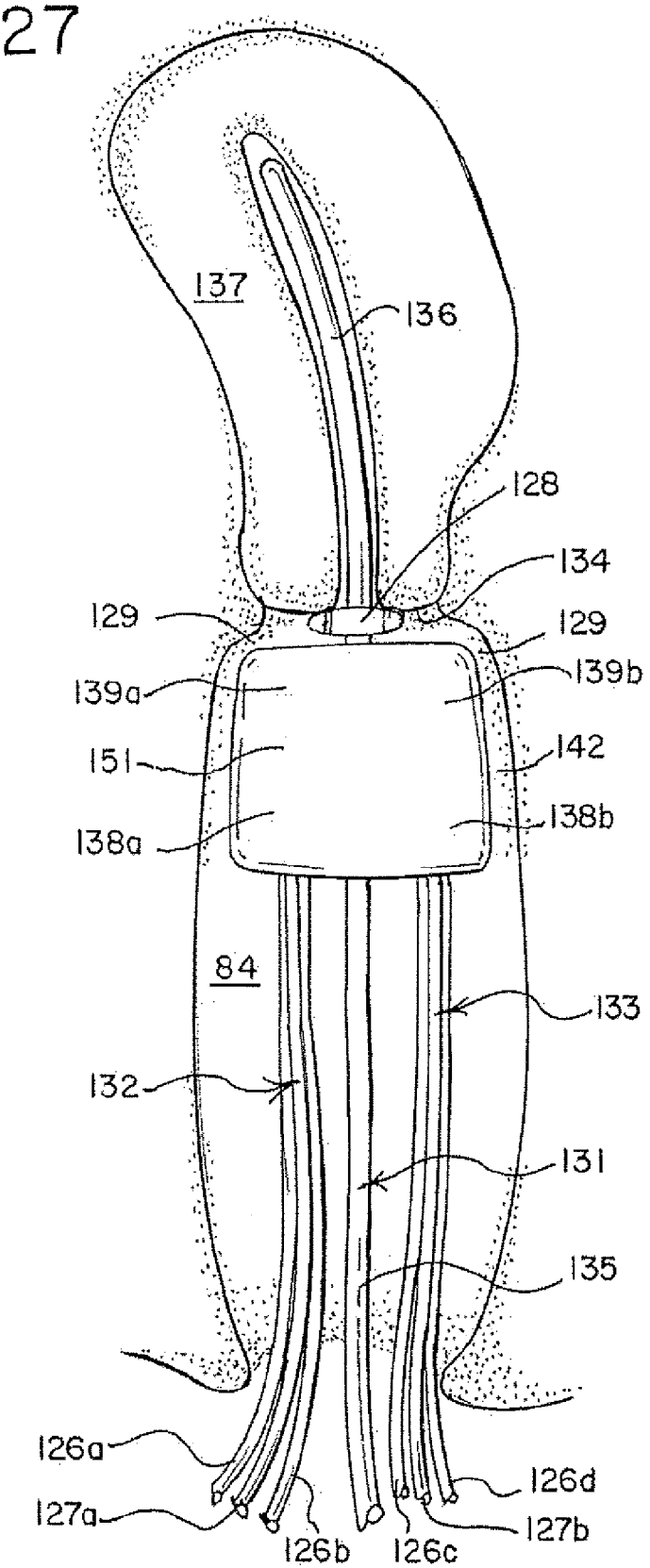
FIG. 27 is a schematic top-view illustration of a tandem and dual ovoid colpostats system having wide-surfaced balloons, as generally shown in FIG. 20.

FIG. 27 is a schematic view in the nature of a perspective top view of an inserted system of tandem and ovoid colpostats similar to FIG. 18, but including wide-surface balloon 151 of FIG. 20. In the orientation illustrated in this FIG. 27, a "pillow" type of balloon is implemented. In this illustrated orientation, the posterior left of balloon 151 and the posterior right engage the uterine wall and expand same so as to push on the rectum of the patient and thus move same away from the colpostat and the radiation emission. Anterior left of balloon 151 and its anterior right balloon inflate to engage and move a portion of the vaginal wall into the normal bladder space, thereby moving the bladder wall at the general area of these balloons away from the colpostat and its radiation source. Balloon 151 can be filled by a single pathway.

Instead, separate pathways may be provided for filling individual sections of the balloon 151, such as posterior left and right and anterior left and right sections. When such a segmented balloon is used, multiple pathways can be used. For example, pathway 126a fills or otherwise controls size of posterior left balloon section 138a. Pathway 126b fills or otherwise controls anterior left balloon 139a. Lumen 127a attaches to a radiation source such as an HDR source as discussed elsewhere herein. Lumen 127b connects ovoid 137 to a radiation source in a similar manner. Pathway 126c provides inflation liquid or gas to anterior right balloon section 139b, while pathway 126d provides gas or liquid passage into the posterior right balloon section 138b. When desired, multiple such lumens can be controlled by the same source of gas or liquid. For example, lumens 126a and 126c can be connected to the same source channel so that both anterior balloon sections 139a and 139b inflate and deflate in general unison. Similarly, pathways 126b and 126d can be controlled by the same source of gas or liquid in order to generally simultaneously control inflation and deflation of posterior balloon sections 138a, 138b.

Figure 28:
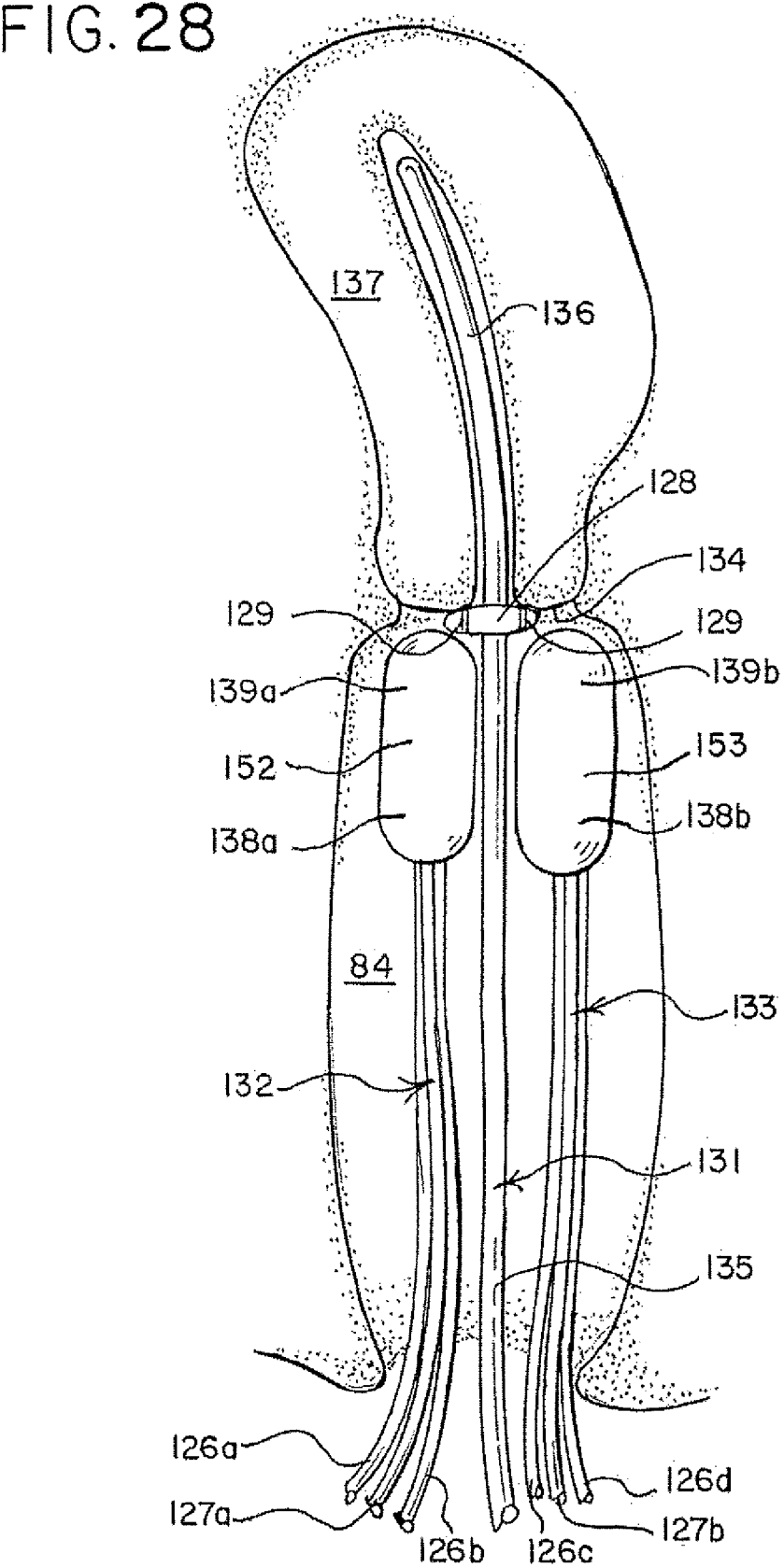
FIG. 28 is a schematic top-view illustration of a tandem and dual ovoid colpostats system having a wide-surfaced balloon, as generally shown in FIG. 21.

FIG. 28 is a schematic view in the nature of a perspective top view of an inserted system of tandem and ovoid colpostats similar to FIG. 18 but including wide-surface balloon 152, 153 of FIG. 21. In the orientation illustrated in this FIG. 28, two "pillow" type of balloons are implemented. In this illustrated orientation, the posterior left of balloon 152 and the posterior right of balloon 153 engage the uterine wall and expand same so as to push on the rectum of the patient and thus move same away from the colpostat and the radiation emission. Anterior left of balloon 152 and anterior right balloon 153 inflate to engage and move a portion of the vaginal wall into the normal bladder space, thereby moving the bladder wall at the general area of these balloons away from the colpostat and its radiation source. Each balloon 152, 153 can be filled by a single pathway.

Instead, separate pathways may be provided for filling individual sections of the balloons 152, 153, such as posterior left and right and anterior left and right sections. When such segmented balloons are used, multiple pathways can be provided. For example, pathway 126a fills or otherwise controls the size of posterior left balloon section 138a. Pathway 126b fills or otherwise controls anterior left balloon section 139a. Lumen 127a attaches to a radiation source such as an HDR source as discussed elsewhere herein. Lumen 127b connects ovoid 137 to a radiation source in a similar manner. Pathway 126c provides inflation liquid or gas to anterior right balloon section 139b, while pathway 126d provides gas or liquid passage into the posterior right balloon section 138b. When desired, multiple such lumens can be controlled by the same source of gas or liquid. For example, lumens 126a and 126c can be connected to the same source channel so that both anterior balloon sections 139a and 139b inflate and deflate in general unison. Similarly, pathways 126b and 126d can be controlled by the same source of gas or liquid in order to generally simultaneously control inflation and deflation of posterior balloon sections 138a, 138b.

In FIG. 27 and FIG. 28, each balloon can be mounted to its ovoid by way of a permanent or removable attachment arrangement. As noted generally herein, the various balloon members are either a permanent component or each can be detachably secured in place. When the former approach is followed, the components all are designed to withstand multiple sterilizations and uses for multiple patients. When the latter approach is used, the balloons and/or individual balloon members are disposable and provided by a supplier in ready-to-use condition.

Several embodiments of ovoid colpostats are shown herein. Each has a distal section or "leg" which typically includes the site at which the radiation emanates during treatment. In some embodiments, one or more of a balloon, a wide-surface balloon, a shield, a detector, a hyperthermia delivery system are associated with or in some cases secured to the colpostat, such as an ovoid distal section. With an embodiment or embodiments, this distal section is attachable and detachable to the rest of the colpostat. Structures and approaches such as those described herein including but not limited to attachment arrangements, detachable members, disposable members and so forth can be applied to or found in tandems, ovoids and/or colpostats. When this embodiment is followed, the distal section of colpostats is a disposable system for single-patient use. Any of these disposable systems can be with one or more of the balloon, wide balloon, shield, detector, and/or hyperthermia components.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. An intrauterine brachytherapy method, comprising:
providing an intrauterine brachytherapy tandem and ovoid colpostat system, the tandem having a tandem proximal section detachable from a tandem distal section having a proximal end;
attaching the tandem proximal section to the proximal end of the tandem distal section to provide an assembled tandem;
inserting the assembled tandem into a patient's uterus;
intracavitarily placing the ovoid within a vagina of said patient, this intracavitary placing being in association with said tandem insertion;
treating by radiation at least one intracavitary location of the patient by way of radiation dosage at the colpostat of the ovoid or tandem; and
detaching the tandem proximal section from the tandem distal section, and removing the ovoid and the tandem proximal section from the patient while retaining the tandem distal section within the uterus of the patient for subsequent treating.

2. The method of claim 1, wherein two colpostats that are ovoids are intracavitarily placed in association with each other, and wherein a space-adjusting balloon is positioned between the two ovoids along their respective lengths within a body cavity of said patient, thereby defining and maintaining a desired distance between the ovoids.

3. The method of claim 1, further including detecting radiation at the balloon during said treating.

4. The method of claim 1, further including providing a hyperthermia subsystem and delivering thermal energy during said treating.

* * * * *